(12) United States Patent
Mutchler

(10) Patent No.: US 7,947,043 B2
(45) Date of Patent: May 24, 2011

(54) INTRAMEDULLARY NAIL AND ASSOCIATED METHOD

(75) Inventor: Austin W. Mutchler, Warsaw, IN (US)

(73) Assignee: Depuy Products, Inc., Warsaw, IN (US)

( * ) Notice: Subject to any disclaimer, the term of this patent is extended or adjusted under 35 U.S.C. 154(b) by 1287 days.

(21) Appl. No.: 10/761,185

(22) Filed: Jan. 20, 2004

(65) Prior Publication Data

US 2006/0095039 A1    May 4, 2006

(51) Int. Cl.
*A61B 17/72* (2006.01)

(52) U.S. Cl. .......................................... 606/64

(58) Field of Classification Search ............... 606/62–68
See application file for complete search history.

(56) References Cited

U.S. PATENT DOCUMENTS

| | | | |
|---|---|---|---|
| 3,716,050 A * | 2/1973 | Johnston | 606/69 |
| 4,622,959 A | 11/1986 | Marcus | |
| 4,678,472 A | 7/1987 | Noiles | |
| 4,790,302 A | 12/1988 | Colwill et al. | |
| 4,875,475 A | 10/1989 | Comte et al. | |
| 5,066,296 A | 11/1991 | Chapman et al. | |
| 5,122,141 A | 6/1992 | Simpson et al. | |
| 5,312,406 A | 5/1994 | Brumfield | |
| 5,480,402 A | 1/1996 | Kim | |
| 5,658,287 A | 8/1997 | Hofmann et al. | |
| 5,658,288 A | 8/1997 | Kim | |
| 5,743,908 A | 4/1998 | Kim | |
| 5,776,194 A | 7/1998 | Mikol et al. | |
| 5,779,704 A | 7/1998 | Kim | |
| 5,814,047 A * | 9/1998 | Emilio et al. | 606/62 |
| 5,935,127 A * | 8/1999 | Border | 606/62 |
| 5,961,555 A | 10/1999 | Huebner | |
| 6,010,506 A | 1/2000 | Gosney et al. | |
| 6,102,953 A | 8/2000 | Huebner | |
| 6,123,708 A | 9/2000 | Kilpela et al. | |
| 6,168,628 B1 | 1/2001 | Huebner | |
| 6,193,758 B1 | 2/2001 | Huebner | |
| 6,221,074 B1 | 4/2001 | Cole et al. | |
| 6,267,785 B1 | 7/2001 | Masin | |
| 6,270,499 B1 | 8/2001 | Leu et al. | |
| 6,277,123 B1 | 8/2001 | Maroney et al. | |
| 6,296,645 B1 * | 10/2001 | Hover et al. | 606/62 |
| 6,319,253 B1 * | 11/2001 | Ackeret et al. | 606/64 |
| 6,379,391 B1 | 4/2002 | Masini | |
| 6,461,360 B1 | 10/2002 | Adam | |

(Continued)

FOREIGN PATENT DOCUMENTS

DE    2004014288 U1    11/2004

(Continued)

OTHER PUBLICATIONS

"Axis". Merriam-Webster Online Dictionary [online], [retrieved on Nov. 16, 2006]. Retrieved from the Internet <URL:www.m-w.com.*

(Continued)

*Primary Examiner* — Eduardo C Robert
*Assistant Examiner* — Jerry Cumberledge

(57) ABSTRACT

An intramedullary nail for use with a first fastener and a second fastener for use in orthopaedic surgery is provided. The nail includes a body defining a longitudinal axis of the body. The body defines an aperture through the body. The aperture has a first portion for cooperation with the first fastener to provide dynamic fixation and a second portion for cooperation with the fastener nail to provide static fixation.

21 Claims, 40 Drawing Sheets

U.S. PATENT DOCUMENTS

| | | |
|---|---|---|
| 6,488,684 B2 * | 12/2002 | Sterghos et al. ............ 606/62 |
| 6,494,913 B1 | 12/2002 | Huebner |
| 6,558,425 B2 | 5/2003 | Rockwood, Jr. |
| 2001/0001821 A1 | 5/2001 | Manderson |
| 2002/0072748 A1 | 6/2002 | Robioneck |
| 2002/0103488 A1 | 8/2002 | Lower et al. |
| 2002/0151897 A1 | 10/2002 | Zirkle, Jr. |
| 2002/0151898 A1 * | 10/2002 | Sohngen et al. ............ 606/62 |
| 2003/0018336 A1 | 1/2003 | Vandewalle |
| 2003/0195515 A1 * | 10/2003 | Sohngen ................ 606/62 |
| 2005/0085812 A1 * | 4/2005 | Sherman et al. ............ 606/61 |
| 2006/0264949 A1 * | 11/2006 | Kohut et al. ................ 606/69 |

FOREIGN PATENT DOCUMENTS

| | | |
|---|---|---|
| JP | 10-501444 | 2/1998 |
| JP | 2001-511040 | 8/2001 |
| JP | 2002-078713 | 3/2002 |
| JP | 2003-521303 | 7/2003 |
| JP | 2003-235861 | 8/2003 |
| WO | WO 97/39693 | 10/1997 |
| WO | WO 00/61018 | 10/2000 |
| WO | WO 00/76414 A1 | 12/2000 |
| WO | WO 03/030770 A2 | 4/2003 |

OTHER PUBLICATIONS

"Thread". Merriam-Webster Online Dictionary [online], [retrieved on Nov. 16, 2006]. Retrieved from the Internet <URL:www.m-w.com.*

"Adjacent". Merriam-Webster Online Dictionary [online], [retrieved on Nov. 16, 2006]. Retrieved from the Internet <URL:www.m-w.com.*

Ace Medical Company—Dynamic Tibial Nailing Surgical Technique, 1996.

Ace Medical Company—AIM Titanium Tibial Nail System Surgical Technique, 1996.

Ace Medical Company—AIM Titanium Tibial Nail System, 1996.

European Search Report dated May 20, 2005 for corresponding EPO Application No. 05250240.8.

* cited by examiner

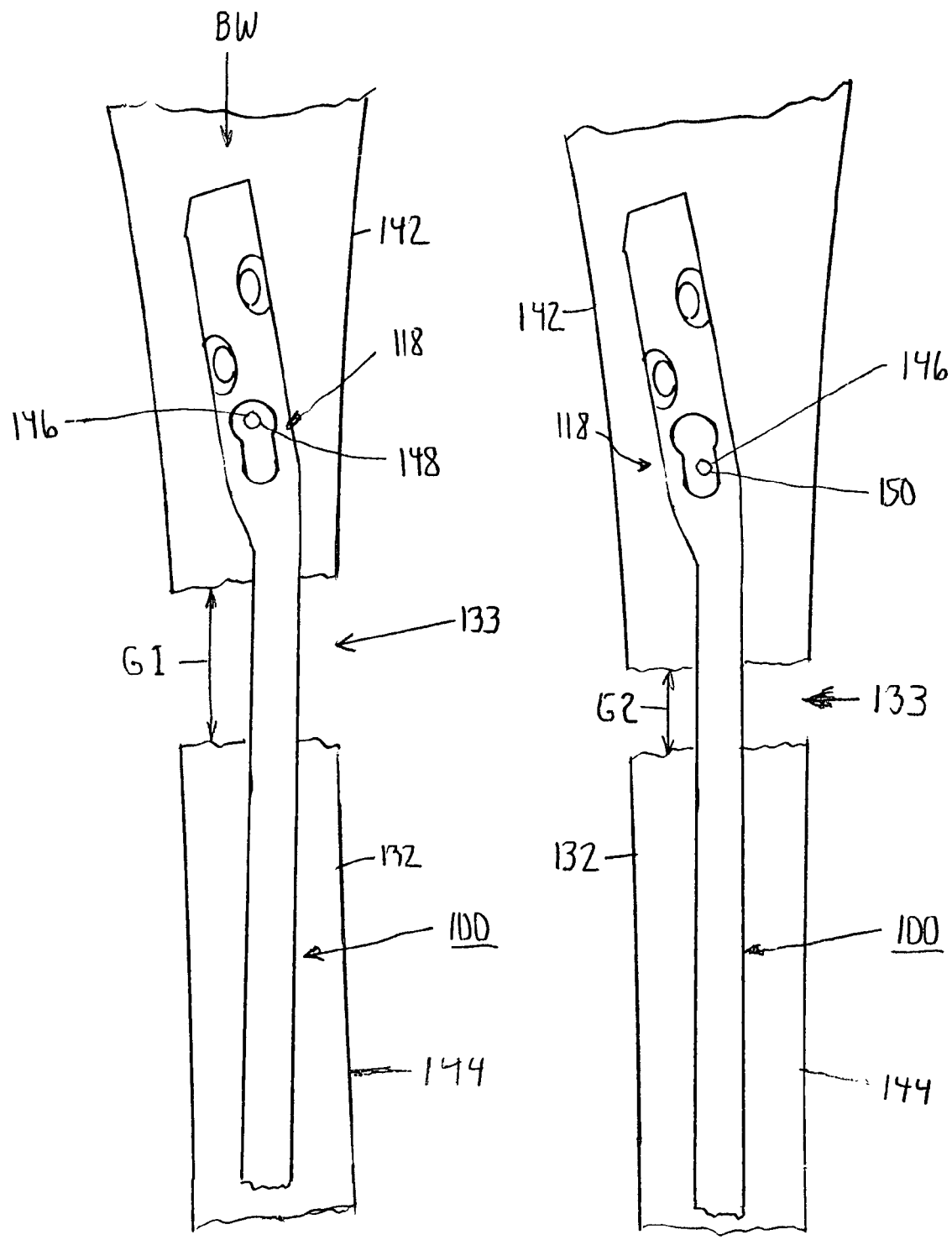

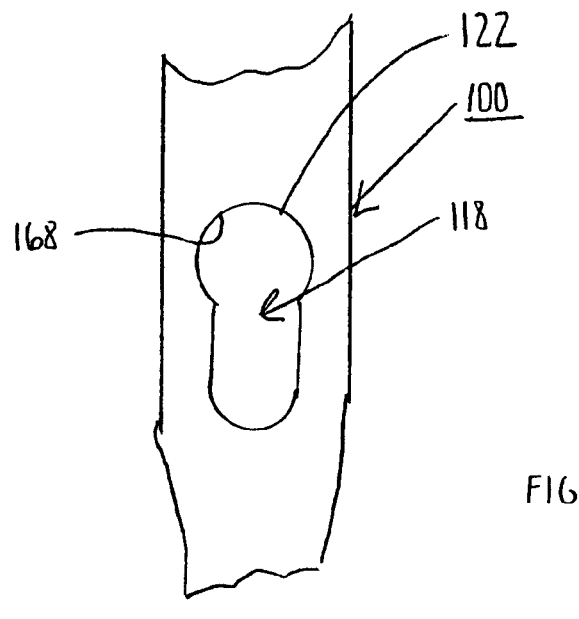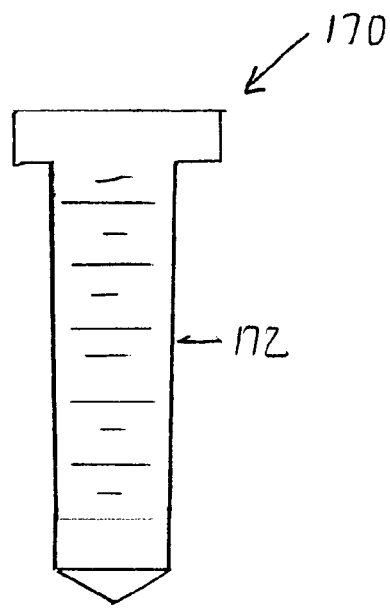
FIG 4A
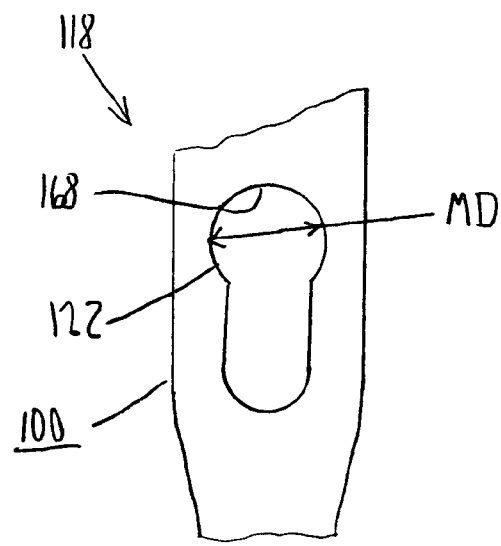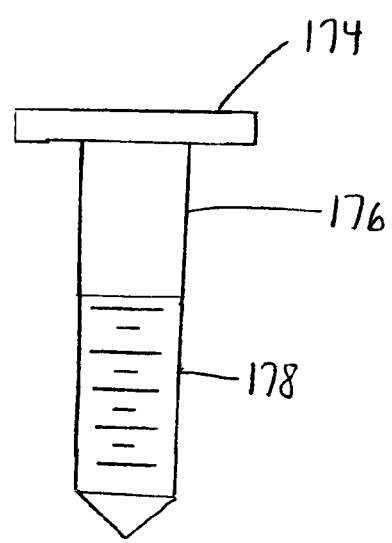
FIG 4B

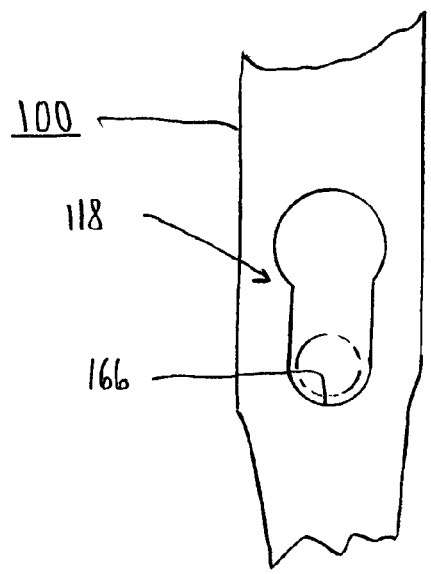
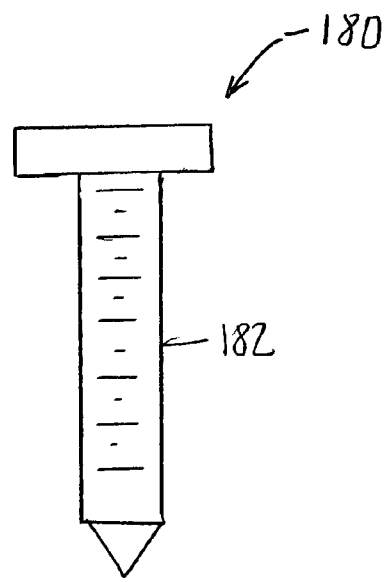
FIG 4C
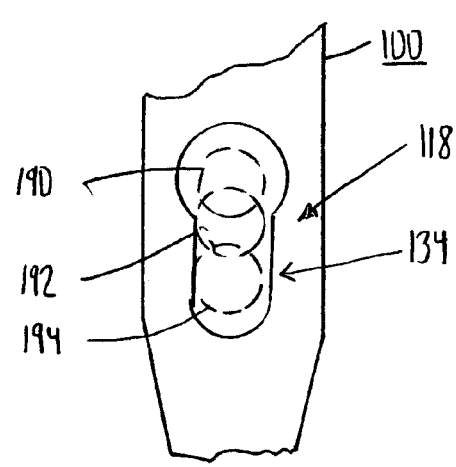
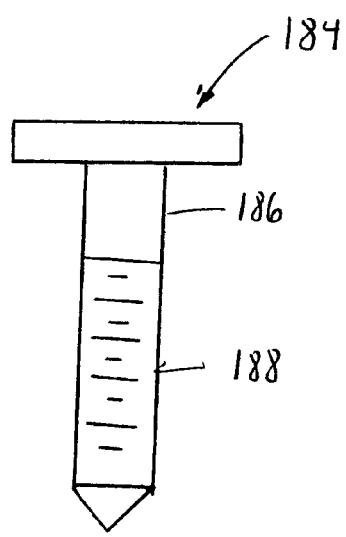
FIG 4D

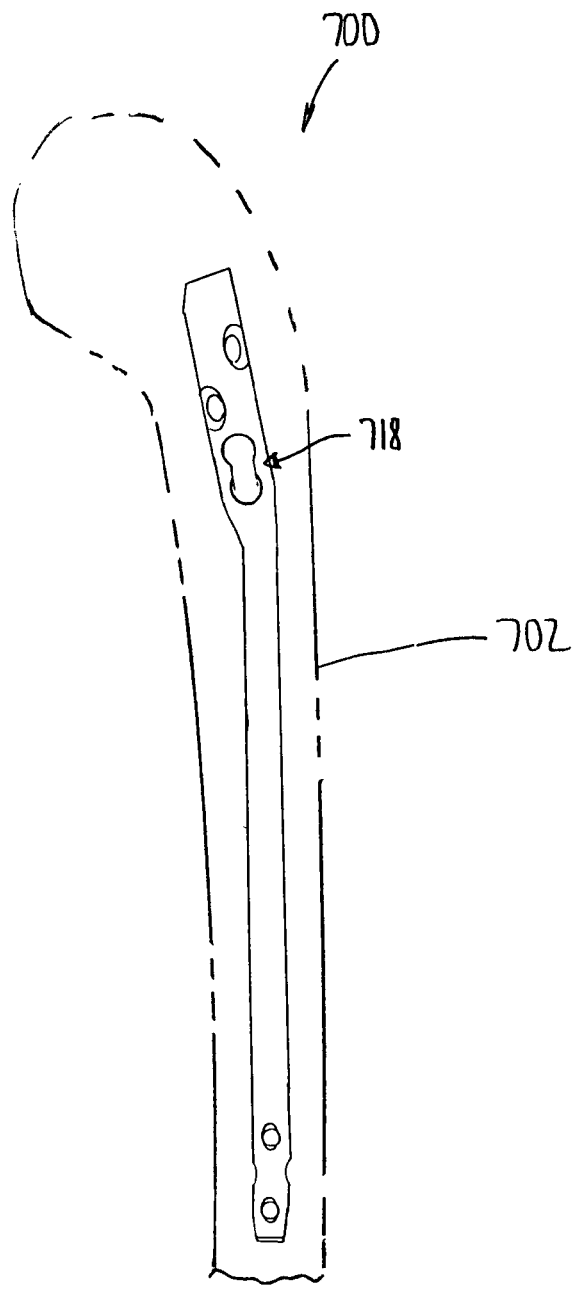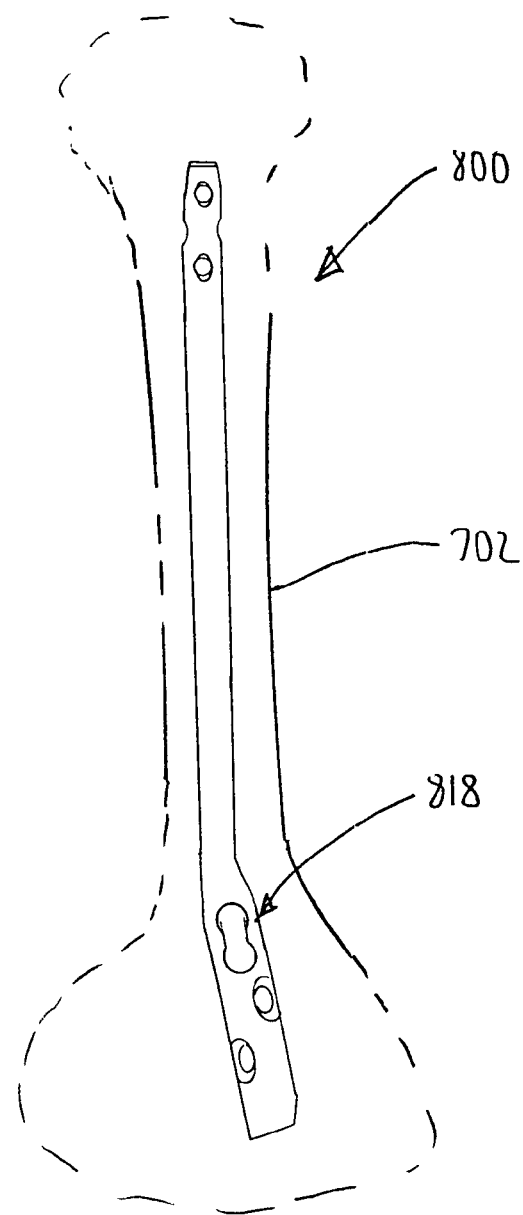
FIG 24
FIG 25

INTRAMEDULLARY NAIL AND ASSOCIATED METHOD

TECHNICAL FIELD OF THE INVENTION

The present invention relates generally to the field of orthopaedics, and more particularly, to an intramedullary nail for use in trauma surgery.

BACKGROUND OF THE INVENTION

The skeletal system includes many long bones that extend from the human torso. These long bones include the femur, fibula, tibia, humerus, radius and ulna. These long bones are particularly exposed to trauma from accidents and as such often are fractured during such trauma and may be subject to complex devastating fractures.

Automobile accidents, for instance, are a common cause of trauma to long bones. In particular, the femur and the tibia frequently fracture when the area around the knee is subjected to frontal automobile accidents.

Often the distal or proximal portions of a long bone, for example, the femur and the tibia are fractured and must be reattached.

Mechanical devices, most commonly in the form of pins, plates, and screws are commonly used to attach fractured long bones. The plates, pins and screws are typically made of a durable material compatible with the human anatomy, for example a metal such as a titanium alloy, a stainless steel alloy, or a cobalt chromium alloy. The plates are typically positioned longitudinally along the periphery of the long bone and have holes or openings through which screws may be inserted into the long bones transversely. Additionally, intramedullary nails or screws may be utilized to secure fractured components of a long bone, for example, the head of a femur.

There are a variety of other devices used to treat femoral fractures. Fractures of the neck, head or intertrochantor of the femur have been successfully treated with a variety of compression screw assemblies, which include, generally, a compression plate having a barreled member, a leg screw, and a compressing screw. The compression plate is secured to the exterior of the femur and the barreled member is inserted into a predrilled hole in the direction of the femoral head. The leg screw, which has a threaded end and a smooth portion, is inserted through the barrel member so that it extends across the break and into the femoral head. The threaded portion engages the femoral head. The compression screw connects the leg screw to the plate. By adjusting the tension of the compressions screw the compression of the fracture can be adjusted. The smooth portion of the leg screw must be free to slide through the barrel member to permit the adjustment of the compression screw.

Subtrochantric and femoral head fractures have been treated with the help of intramedullary rods, which are inserted into the marrow canal of the femur to immobilize the femur parts involved in the fracture. A single angle cross nail or locking screw is inserted through the femur and the proximal end of the intramedullary rod. In some varieties, one or two screws may be inserted through he femoral shaft and through the distal end of the intramedullary rod. The standard intramedullary rods have been successfully employed in treating fractures in lower portions of the femoral shaft.

Intramedullary rods or nails are used by orthopaedic surgeons to treat fractures involving long bones such as the femur, humerus, tibia, fibula, etc. The medullary canal of the fractured bone is drilled out or otherwise opened from one end and the intramedullary nail and is longitudinally placed within the medullary canal to contact at least two fragments, i.e., such that the nail extends on both sides of the fracture. As used herein, the term fragment, refers to a portion of a fractured bone regardless of whether the fracture is complete. When implanted, the nail strengthens and supports fragments of the fractured bone during healing of the fracture.

Various types of intramedullary rods or nails are well known within the medical device arts, and several different methods have used to attach the intramedullary nail within the bone. For instance, in U.S. Pat. No. 4,338,926 to Kummer, et al, an intramedullary nail is disclosed which places a compressive force regularly outside of the interior wall of the cortex structure surrounding the intramedullary nail. The compressive force secures the Kummer nail within the medullary canal of the fragments.

Similarly, in U.S. Pat. No. 4,457,301 to Walker a flexible plastic core element holds longitudinal pins of intramedullary nail in place. In U.S. Pat. No. 5,514,137 to Coutts, cement is injected through a cannula in an intramedullary nail to secure the distal end of the intramedullary nail to a bone. The medullary nail designs may employ a more secure and mechanically positive attachment to the bone, such as through use of one or more fasteners, which extend transversally to the longitudinal axis of the nail and through the cortex of the bone.

The bone fastener is received within a receiving recess or through the hole within the intramedullary nail to secure the intramedullary nail relative to the bone fastener. In the transverse attachment, the receiving opening defines an axis, which is at an angle to the longitudinal axis of the nail; 90 degrees and 45 degrees are common. The bone fastener is attached onto this receiving opening axis.

U.S. Pat. No. 4,733,654 to Morino, U.S. Pat. No. 5,057,110 to Krantz, et al, U.S. Pat. No. 5,127,913 to Thomas, Jr., U.S. Pat. No. 5,514,137 to Coutts and others disclose such a transverse bone fastener attachment in a bicordical attachment. U.S. Pat. No. 5,454,438 to Penning, shows a nail design with a recess, which permits only unicordical attachment. The present invention relates particularly to intramedullary nails, which use bone fasteners through the cortex for attachment.

Intramedullary nails are secured in the medullary canal by use of the fasteners to connect the nail to the cortical bone of the long bone. The attachment of the nail to the bone may be accomplished by one of two alternate methods. The first method is static locking in which the nail is rigidly secured to the screw and to the cortical bone. Such static locking provides for a secure attachment of the nail to the bone and promotes initial healing of the fracture site.

Due to a phenomenon often referred to as Wolff's law, the healing over time of bone around a fracture site is promoted if the fracture site is under load or stress. This phenomenon known as Wolff's law is due to the fact that if the bone at the fracture site is not under load, the bone tends to atrophy. The use of the static locking method therefore reduces the load at the fracture site and may subject the fracture site to atrophy. For such reasons, an alternate locking method may be desired.

Such an alternate locking method is known as a dynamic locking. Under dynamic locking, the fastener is movably secured to the opening of the intramedullary nail. Such movement may be accomplished by permitting the fastener to move along the axis of the opening or by providing an elongated opening in which the fastener may move with respect to the IM nail.

More recently, medullary nails have been designed which include a resorbable material positioned in the openings in which the fasteners are inserted for securing the nail through the bone. In such configuration, the intramedullary nail at the time of surgery operates in the static locking method and as the fracture site begins to heal, the body resorbs the resorbable material and the fastener is permitted to move with respect to the intramedullary nail. Such a nail with a resorbable insert is shown in U.S. Pat. No. 6,296,645 to Hover, et al, hereby incorporated by reference in its entireties.

To provide for an option for the surgeon to provide for static and dynamic locking for the same intramedullary nail, intramedullary nails have been designed with slots elongated in the longitudinal direction of the intramedullary nail. With such intramedullary nail slots, the nail may be used in a dynamic mode by placing the screw centrally in the slot or may be used in a static mode by positioning the fastener at the distal end of the slot. When used in a static mode, the nail can only be positioned in static mode in one position. The condition of the bone may be such that the position available for static locking may not be possible due to damage to the bone at that position.

The present invention is designed to overcome at least one of the aforementioned problems.

SUMMARY OF THE INVENTION

According to the present invention, an intramedullary nail is provided with a slot. The nail can be locked in a dynamic mode with a standard cortical screw. The nail can also be locked in a static mode using a larger shaft screw through either the proximal or the distal end of the slot. In one aspect of the present invention, the ends of the slot may be threaded so that a cortical screw could be threaded into the slot therefore locking the nail into the static mode.

The present invention provides for a nail with a slot that has an enlarged hole at an end of the slot. In one aspect of the present invention, the enlarged holes are at both ends of the slot. A shaft screw can be inserted through the enlarged end locking the nail in static mode. If dynamization is desired, a standard cortical screw of smaller diameter to the shaft screw can be inserted into the slot. In one other variation of the invention, the enlarged end or ends of the slot may be threaded so a cortical screw can be threaded into the slot, therefore locking the nail in static mode.

According to one embodiment of the present invention, there is provided an intramedullary nail for use with a first fastener and a second fastener for use in orthopaedic surgery. The nail includes a body defining a longitudinal axis of the body. The body defines an aperture through the body. The aperture has a first portion for cooperation with the first fastener to provide dynamic fixation and a second portion for cooperation with the second fastener to provide static fixation.

According to another embodiment of the present invention there is provided a kit for use in orthopaedic surgery. The kit includes a first fastener, a second fastener, and an intramedullary nail. The nail includes a body defining a longitudinal axis of the nail. The body defines an aperture through the body. The aperture has a first portion for cooperation with the first fastener to provide dynamic fixation and having a second portion for cooperation with the second fastener to provide static fixation.

According to a further embodiment of the present invention, there is provided a method for use in orthopaedic surgery. The method includes the step of providing an orthopaedic surgery kit including a first fastener, a second fastener, and an intramedullary nail. The nail has a body defining a longitudinal axis of the nail. The body defines an aperture through the body. The aperture has a first portion for cooperation with the first fastener to provide dynamic fixation and has a second portion for cooperation with the second fastener to provide static fixation.

The method further includes the steps of cutting an incision in the patient, preparing a bone cavity and inserting the nail into the cavity. The method further includes the step of choosing one of static fixation and dynamic fixation for the surgery. The method also includes the step of selecting one of the first fasteners and the second fastener based on the choice of one of static fixation and dynamic fixation for the surgery. The method further includes the step of securing the chosen one of the first fastener and the second fastener into the nail.

According to a yet another embodiment of the present invention, there is provided an intramedullary nail for use in orthopaedic surgery. The nail includes a body defining a longitudinal axis and a transverse axis. The transverse axis is normal to the longitudinal axis. The body defines an aperture in the body. The aperture is substantially longer in the longitudinal axis than in transverse axis. The aperture defines an enlarged portion thereof along the longitudinal axis.

The technical advantages of the present invention include the ability to obtain locked and unlocked configurations with the same intramedullary nail. For example, according to one aspect of the present invention an elongated slot is provided in an intramedullary nail with threads on a portion of the slot. Thus, the present invention provides for an ability to obtain locked and unlocked configurations with the same intramedullary nail.

The technical advantages of the present invention further include the ability to obtain static and dynamic configurations with the same intramedullary nail. According to one aspect of the present invention, an intramedullary nail is provided with an elongated slot having threads on part of the slot with a resorbable member positioned in a portion of the slot. The fastener may be positioned in the slot and engage with the threads on the slot to provide for a static configuration. Conversely, a fastener may be engaged in the resorbable member within the slot to provide for a dynamic configuration. Thus, the present invention provides for static dynamic configurations within the same intramedullary nail.

Another technical advantage of the present invention includes the ability to obtain two locked portions within the same slot on an intramedullary nail. For example, according to one aspect of the present invention, an intramedullary nail is provided with a slot having spaced apart threaded portions. A fastener may be positioned in either one of the first and second threaded portions of the intramedullary nail. Thus, the present invention provides for two locked portions within the same slot of an intramedullary nail.

The technical advantages of the present invention further include the ability to obtain a dynamic configuration in an intramedullary nail with limited motion. For example, according to one aspect of the present invention, an intramedullary nail is provided with a slot with a large round portion filled with a resorbable material. The fastener is positioned in the resorbable material and is permitted to move over time as the resorbable material resorbs within the round portion of the slot. The round portion of the slot limits the motion during the dynamization. Thus, the present invention provides for the intramedullary nail, which provides for dynamization with a limited linear motion.

The technical advantages of the present invention further include the ability to obtain dynamization with extended motion. For example, according to another aspect of the present invention, an intramedullary nail is provided with a slot having a small screw, which may move substantially longitudinally along the slot. The slot may be filled completely with resorbable material, which resorbs over time, permitting the motion of the screw along the slot of the nail. Thus, the present invention provides for an intramedullary nail, which may obtain an extended, linear motion during dynamization.

The technical advantages of the present invention further include the ability to provide an intramedullary nail, which may provide for a locked configuration that is locked both radially and longitudinally. For example, according to one aspect of the present invention, an intramedullary nail is provided with a threaded portion of the slot to mate with the fully threaded shaft of a screw. Thus, the present invention provides for intramedullary nail with a locked configuration for locking the intramedullary nail to the bone, both radially and longitudinally.

The technical advantages of the present invention further include the ability to obtain a locked configuration longitudinally and an unlocked radial configuration. For example, according to one aspect of the present invention, an intramedullary nail is provided with a threaded portion of the slot that is in sliding engagement with an unthreaded shaft portion of a partially threaded screw. Thus, the present invention provides for an intramedullary nail with a radial unlocked configuration and a longitudinally locked configuration.

The technical advantages of the present invention further include the ability to obtain a partially controlled dynamization. For example, according to one aspect of the present invention, an intramedullary nail is provided with a slot having a resorbable member only positioned in the threaded portion of the slot. After the resorbable material has been resorbed, the fastener may slide along the entire length of the slot. Thus, the present invention provides for an intramedullary nail with partially controlled dynamization.

The technical advantages of the present invention also include the ability to obtain fully controlled dynamization. For example, according to an aspect of the present invention, an intramedullary nail is provided with a slot with resorbable material on substantially the entire slot. A fastener is secured into the resorbable material of the slot. As the slot resorbs, the dynamization of the intramedullary nail may occur through the entire length of the slot. Thus, the present invention provides for an intramedullary nail with a fully controlled dynamization.

Other technical advantages of the present invention will be readily apparent to one skilled in the art from the following FIGS., descriptions and claims.

BRIEF DESCRIPTION OF THE DRAWINGS

For a more complete understanding of the present invention and the advantages thereof, reference is now made to the following description taken in connection with the accompanying drawings, in which:

FIG. 1C is a partial plan view of the intramedullary nail of FIG. 1 in a long bone prior to dynamization;

FIG. 1D is a partial plan view of the intramedullary nail of FIG. 1 in a long bone after dynamization;

FIG. 4A is a partial plan view of the intramedullary nail of FIG. 1 with a large fully threaded fastener for use with the nail;

FIG. 4B is a partial plan view of the intramedullary nail of FIG. 1 with a large partially threaded fastener for use with the nail;

FIG. 4C is a partial plan view of the intramedullary nail of FIG. 1 with a smaller fully threaded fastener for use with the nail;

FIG. 4D is a partial plan view of the intramedullary nail of FIG. 1 with a smaller partially threaded fastener for use with the nail;

FIG. 20 is a partial plan view of the intramedullary nail of FIG. 7 with the aperture filled with a resorbable material;

FIG. 21A is an enlarged partial plan view of the intramedullary nail and fastener assembly of FIG. 21 showing the movement of the fastener during resorbsion and dynamazation;

FIG. 24 is a plan view partially in cross section of the intramedullary nail of the present invention showing the nail in position in a femur in the form of a femoral nail;

FIG. 25 is a plan view partially in cross section of the intramedullary nail of the present invention showing the nail in position in a femur in the form of a retrograde nail;

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 1:
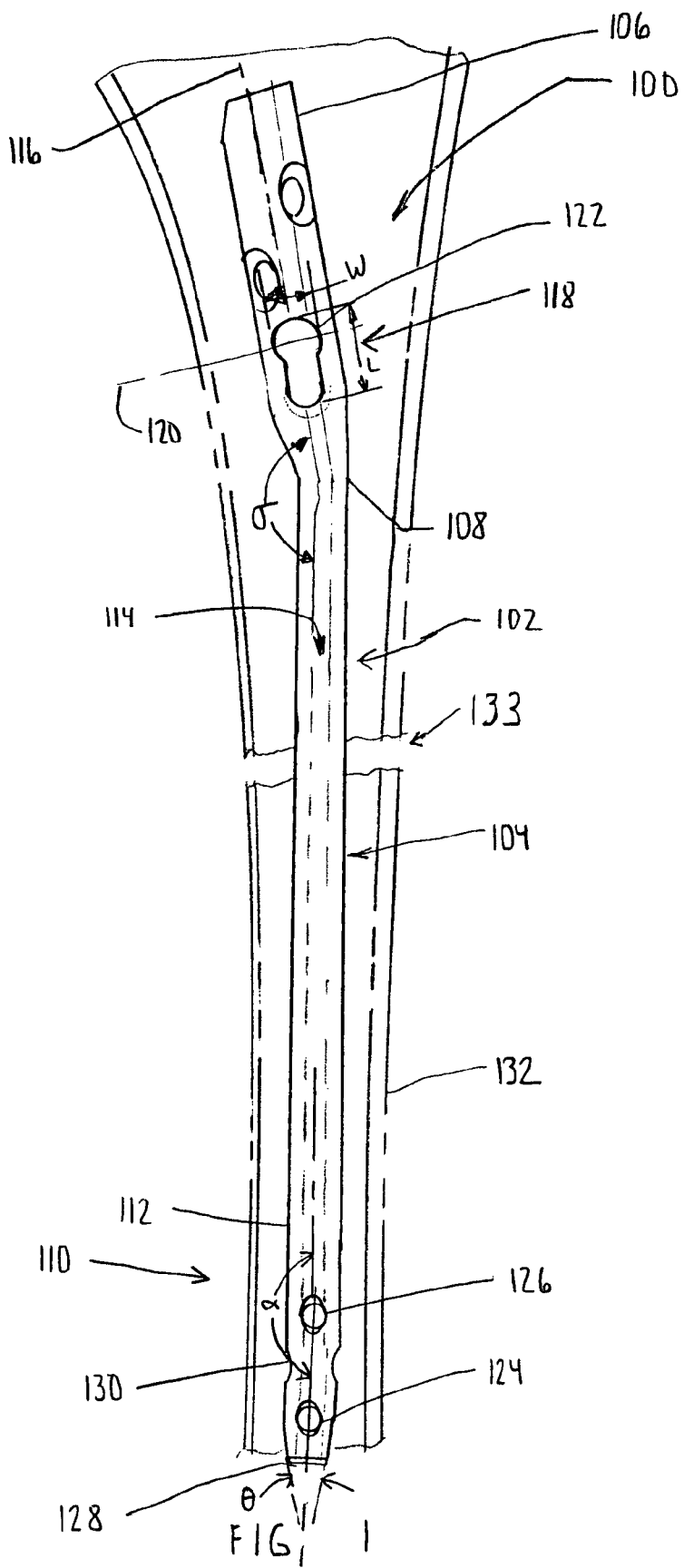
FIG. 1 is a plan view of an intramedullary nail in accordance with an embodiment of the present invention.

According to the present invention and referring now to FIG. 1, an intramedullary rod or nail 100 is shown for use in orthopaedic surgery. The nail 100 includes a body 102. The body 102 is elongated and may, for example, have a generally uniform cross-section and extend uniformly along its length. Alternatively, and as shown in FIG. 1, the body 102 may have a nonlinear shape to conform to the nonlinear shape of a long bone. For example as shown in FIG. 1, the body 102 includes a central portion 104 and a proximal portion 106 extending outwardly from first end 108 of the central portion 104. A distal portion 110 may extend outwardly from second end 112 of the central portion 104.

The body 102 may have any suitable shape and may, for simplicity, be generally cylindrical. The body 102 may be solid or may, as shown in FIG. 1, be hollow or cannulated having a central longitudinal cannula or central opening 114. The proximal portion 106 of the body 102 may extend at an angle, for example angle σ, of approximately 160° from the first end 108 of the central portion 104 of the body 102. The proximal portion 106 may define a proximal portion centerline 116.

According to the present invention, the body 102 defines an aperture 118 passing through the body 102. It should be appreciated that the aperture 118 may be positioned anywhere along the body 102. For example, the aperture 118 may be positioned in the central portion 104, the distal portion 110, or the proximal portion 106. As shown in FIG. 1, the aperture 118 is positioned in the proximal portion 106 of the body 102.

As shown in FIG. 1, the aperture 118 has a length L, which is substantially longer than the width W of the aperture 118. In other words, the aperture 118 is substantially longer in the direction of longitudinal axis 116 than in transverse axis 120, normal to the longitudinal axis 116.

As shown in FIG. 1, the aperture 118 defines an enlarged portion 122 of the aperture 118. The proximal portion 106 and the central portion 104 of the body 102 may have any suitable shape and for simplicity may be generally cylindrical and may be hollow or cannulated defined by the opening 114.

The distal portion 110 of the body 102 may have any suitable shape and may, as shown in FIG. 1, extend at, for example, an angle α of for example 170° from the central portion 104 of the body 102. The distal portion 110 may have a generally cylindrical shape and be cannulated and defined by the central opening 114. The distal portion may include a first distal cross-hole 124 as well as a second spaced apart distal cross-hole 126. The distal portion 110 may include a tip 128 which is tapered and defined by an angle θ. The angle θ may be, for example, 25°.

Distal portion 110 may further include an anterior/posterior hole recess 130. The hole 130 serves to cooperate with additional fasteners (not shown).

The first distal cross-hole 124 in the second distal cross-hole 126 may be utilized with fasteners (not shown) to assist in securing the nail 100 to, for example, tibia 132.

As shown in FIG. 1, the intramedullary nail 100 may be used with, for example, the tibia 132. The tibia 132 may have a fracture site 133, which is, for example, located adjacent the central portion 104 of the nail 100. The fracture site 133 may be a complete fracture and may have a distraction gap or a space between the adjacent portions of the fracture.

Figure 1A:
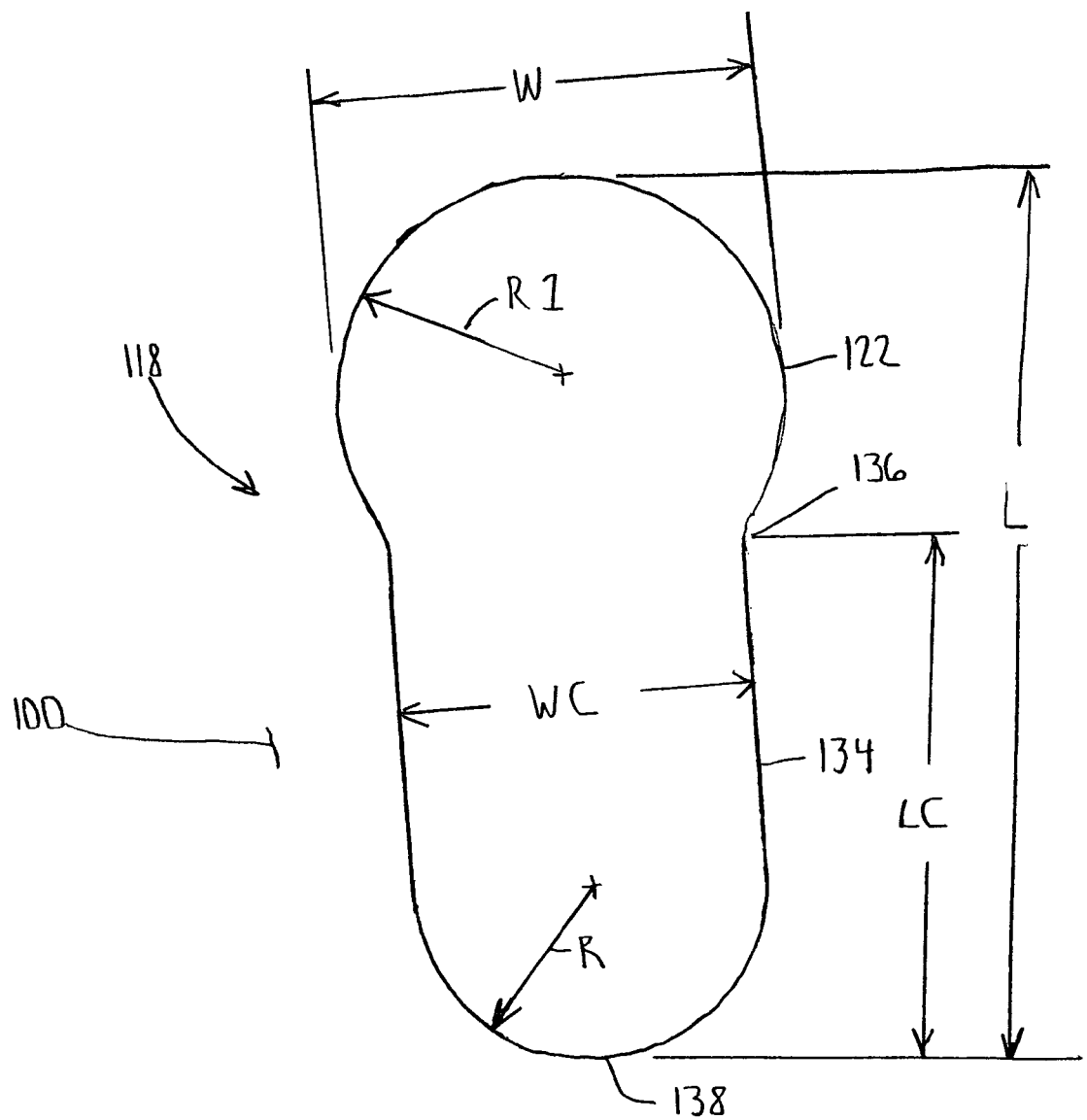
FIG. 1A is a partial plan view of the aperture of the intramedullary nail of FIG. 1 in accordance with an embodiment of the present invention.

Referring now to FIG. 1A, the aperture 118 is shown in greater detail. It should be appreciated that the aperture 118 preferably extends through both walls of the proximal portion 106 of the body 102. For example, as shown in FIG. 1A, the aperture 118 includes a generally rectangular central section 134. The central section 134 may define a central section length LC as well as central section width WC. The length LC may be larger than the width WC. The length LC of the rectangular central section 134 extends from proximal end 136 to distal end 138 of the central section 134.

For cooperation with a cylindrically shaped fastener (not shown) the end, for example distal end 138 of the central section 134, may be arcuate or semicircular. The distal end 138 may be defined, for example, by a radius R.

According to the present invention, the aperture 118 includes the enlarged portion 122. The enlarged portion 140 may be positioned anywhere along the aperture 118. For example the enlarged portion 122 may extend proximally from distal end 138 of the rectangular section 134. The enlarged portion 134 may have a generally cylindrical shape defined by radius R1.

Figure 1B:
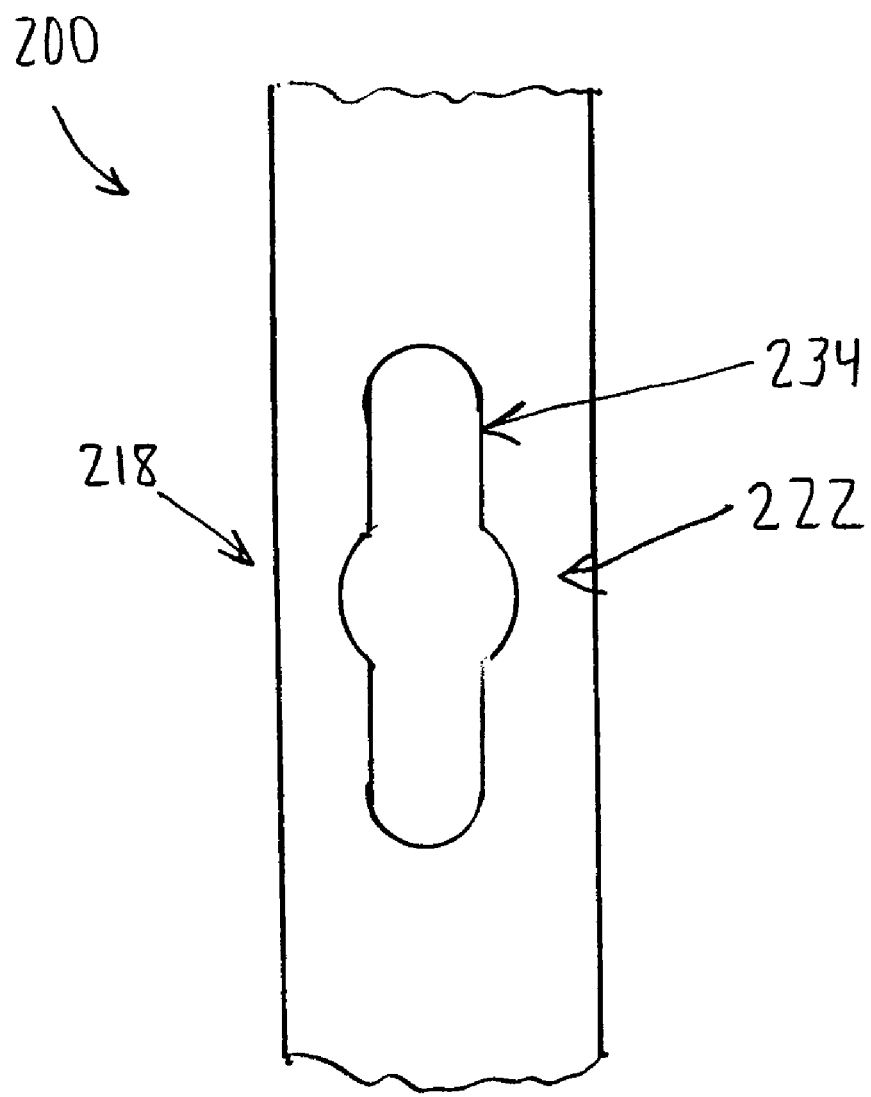
FIG. 1B is a partial plan view of an aperture of an intramedullary nail in accordance with another embodiment of the present invention.

Referring now to FIG. 1B, another embodiment of the present invention is shown as intramedullary nail 200. Intramedullary nail 200 is similar to intramedullary nail 100 of FIG. 1 except that intramedullary nail 200 includes an aperture 218 which is somewhat different than the aperture 118 of intramedullary nail 100. For example, the intramedullary nail 200 of FIG. 1B includes an enlarged portion 222 of the aperture 218, which is positioned centrally within rectangular central section 234 of the aperture 218.

Referring now to FIG. 1C, fracture site 133 of the tibia 132 with intramedullary nail 100 of the present invention is shown. It should be appreciated that the surgeon, while performing trauma surgery on a fractured bone, will set the bone and reduce the fracture or minimize the distraction gap. It should be appreciated that a distraction gap, for example gap G1 as shown in FIG. 1C, will exist between upper portion 142 of the tibia 132 and lower portion 144 of the tibia 132.

Referring to FIG. 1C, a fastener 146 may be positioned in aperture 118. The fastener 146 may be positioned proximately in the slot 118 as shown in FIG. 1C. The patient's body weight (BW) generates a force downwardly on the upper portion 142 of the tibia 132. As dynamization occurs, the distraction gap G1 narrows or the upper portion 142 of the tibia 132 moves toward the lower portion 144 of the tibia 132.

Referring now to FIG. 1D, the distraction gap G2 is shown after a period of dynamization. The distraction gap of FIG. 1D is defined by a dimension G2 that is less than the distraction gap G1 of FIG. 1C. Also it should be appreciated that the fastener 146 has moved from the first position 148 to a second position 150, for example, centrally located in the aperture 118 of the nail 100. It should be appreciated that to provide for dynamization, an upper initial position of the fastener 146 in the aperture 118 is preferred.

Figure 2:
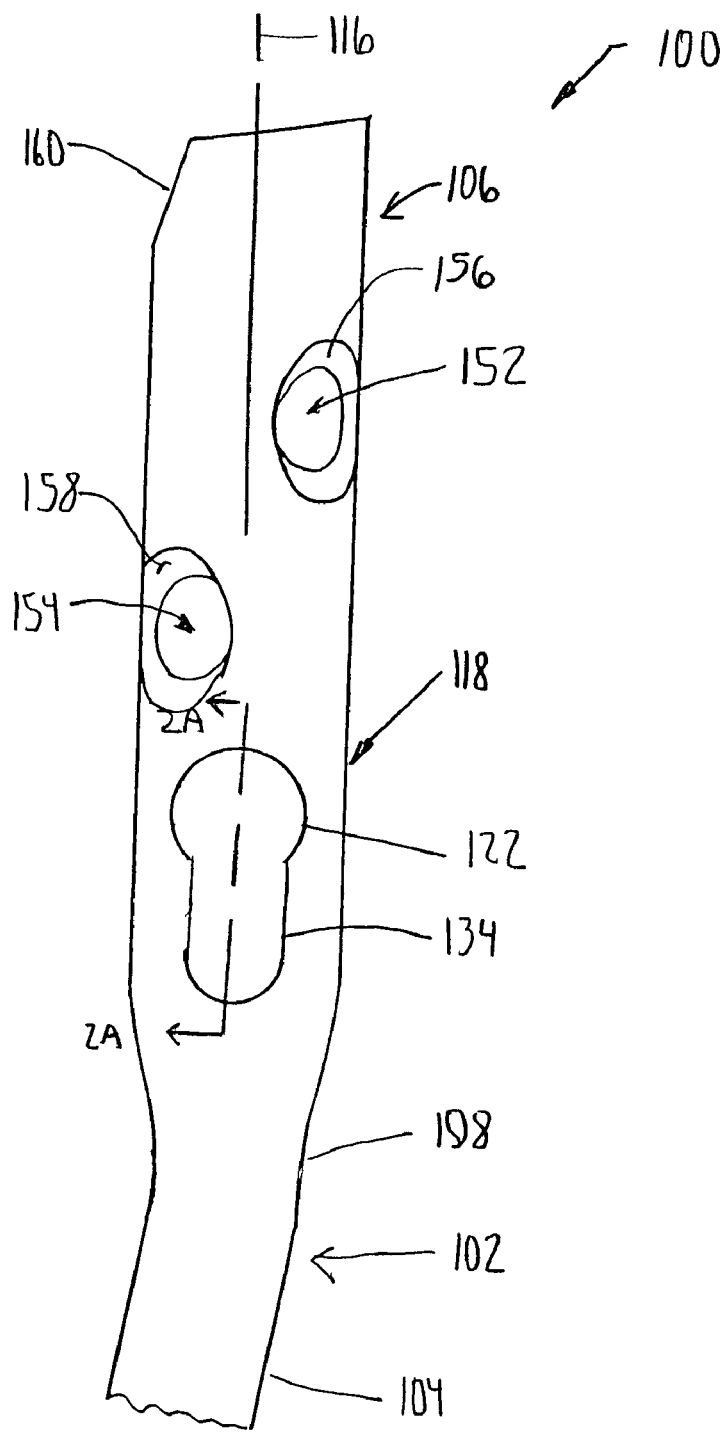
FIG. 2 is an enlarged partial plan view of the intramedullary nail of FIG. 1 showing an end of the nail in greater detail.

Referring now to FIG. 2, the proximal portion 106 of the intramedullary nail 100 is shown in greater detail. As shown in FIG. 2, the aperture 118 is located in the proximal portion 106 of the nail 100. The aperture 118 includes the rectangular central section 134 and the enlarged cylindrical portion 122. While it should be appreciated that the proximal portion 106 of the body 102 of the nail 100 may include only the aperture 118 for securing a fastener, it should be appreciated that additional features may be provided in the nail 100 for cooperation with fasteners.

For example, and as shown in FIG. 2, the proximal portion 106 of the nail 100 may also include a first proximal cross-hole 152. The first proximal cross-hole 152 may as shown in FIG. 2 be positioned proximal to the aperture 118. The proximal portion 106 of the body 102 of the nail 100 may further include a second proximal cross-hole 154. The second proximal cross-hole 154 may for example be positioned between the first proximal cross-hole 152 and the aperture 118. The first proximal cross-hole 152 and the second proximal cross-hole 154 may optionally include chamfers 156 and 158, respectively, for guiding the fastener into the holes 152 and 154.

Additional features may be provided on, for example, the proximal portion 106 of the body 102 of the nail 100. For example a flat 160 may be positioned at the proximal end of the proximal portion 106 for providing clearance for soft tissues, for example, a tendon or a ligament.

Figure 2A:
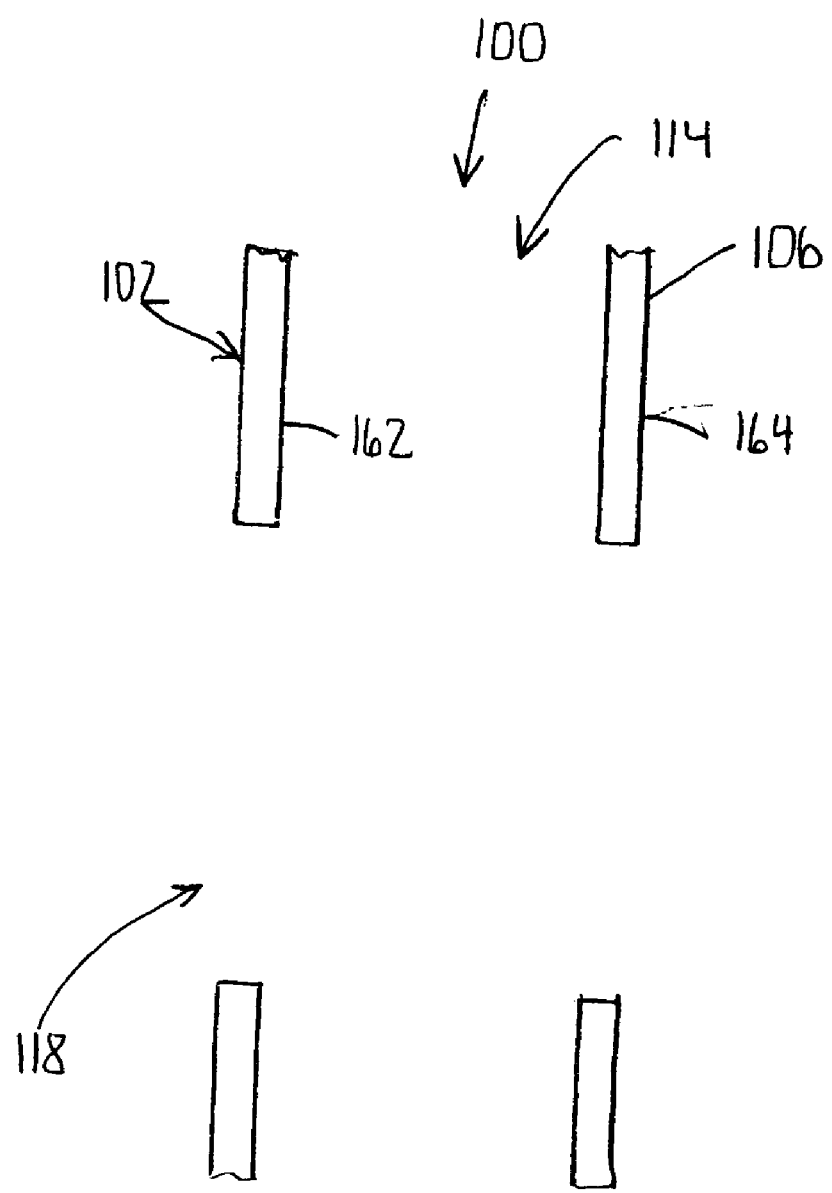
FIG. 2A is partial cross sectional view of FIG. 2 along the lines 2A2A in the direction of the arrows.

Referring now to FIG. 2A the aperture 118 is shown in greater detail in the proximal portion 106 of the body 102 of the nail 100. The aperture 118 extends through first wall 162 as well as second wall 164 of the body 102 of the nail 100.

Figure 2B:
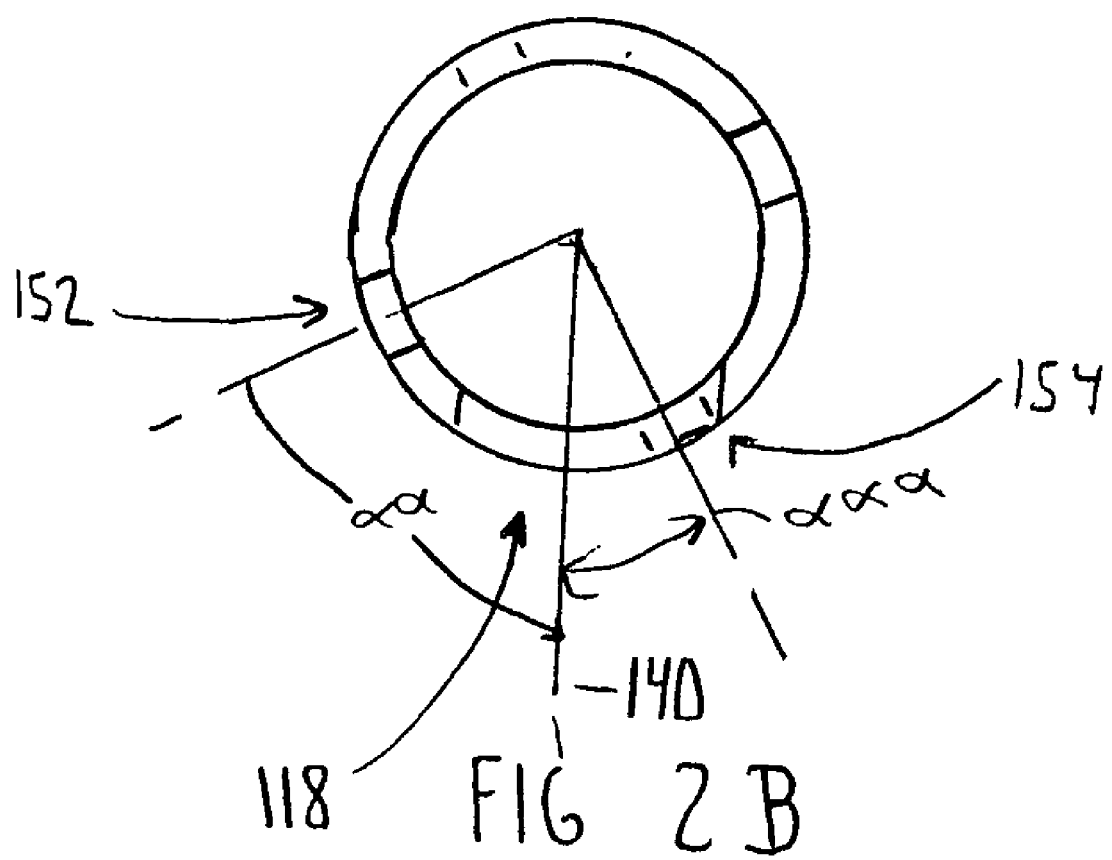
FIG. 2B is a top view of FIG. 2.

Referring now to FIG. 2B, the first cross-hole 152 and the second proximal cross-hole 154 are shown passing through both first and second walls of the cannulated nail 100. The cross-holes 152 and 154 may be angularly positioned with respect to the aperture 118 for providing optimal positioning for the fasteners. For example, the first cross-hole 152 may be positioned at an angle αα from centerline 140 of the slot or aperture 118. Similarly, the second proximal cross-hole 154 may be positioned at an angle ααα from the aperture centerline 140 of the aperture 118.

Figure 2C:
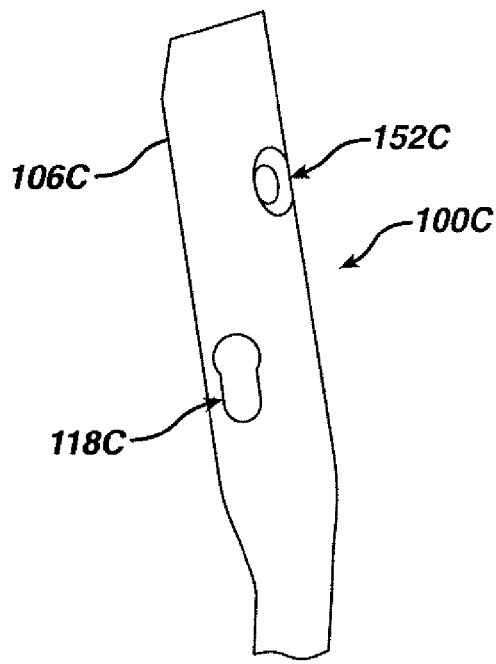
FIG. 2C is a partial plan view of another embodiment of the presentation showing a nail with a proximal cross-hole.

According to the present invention and referring now to FIG. 2C, another embodiment of the present invention is shown as intramedullary nail 100C. The nail 100C is similar to the nail 100 of FIG. 2 except that the proximal portion 106C of the nail 100C includes a solitary proximal cross-hole 152C in addition to the aperture 118C.

Figure 2D:
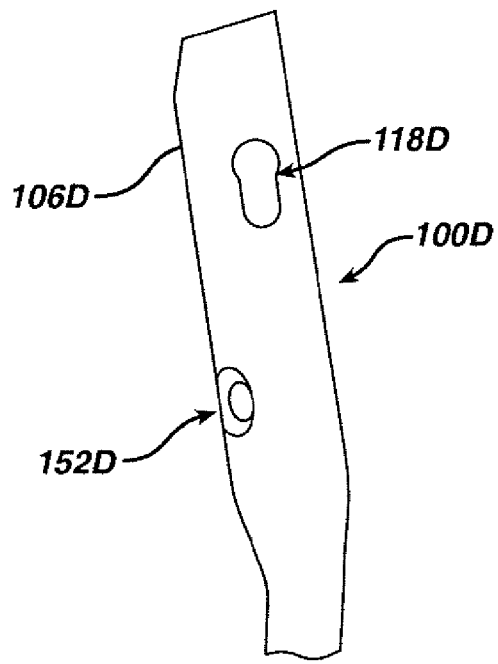
FIG. 2D is a partial plan view of another embodiment of the present invention showing a nail with a distal cross-hole.

Referring now to FIG. 2D, another embodiment of the present invention is shown as intramedullary nail 100D. The intramedullary nail 100D is similar to the nail 100 of FIG. 2 except that the proximal portion 106D of the nail 100D includes a solitary proximal cross-hole 152D that is positioned distally from the aperture 118D.

Figure 2E:
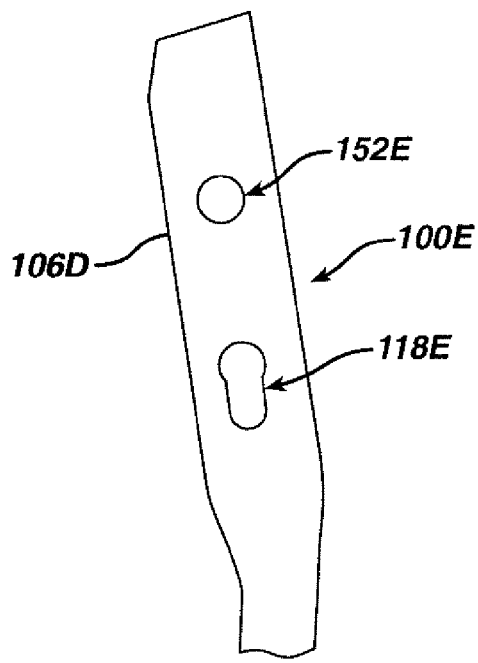
FIG. 2E is a partial plan view of another embodiment of the present invention showing a nail with proximal cross-hole in alignment with the aperture.

Referring now to FIG. 2E, another embodiment of the present invention is shown as intramedullary nail 100E. The intramedullary nail 100E is similar to the nail 100 of FIG. 2 except that the nail 100E includes a proximal cross-hole 152E that is in radial alignment with the aperture 118E. The proximal cross-hole 152E is positioned proximally with respect to the aperture 118E.

Figure 2F:
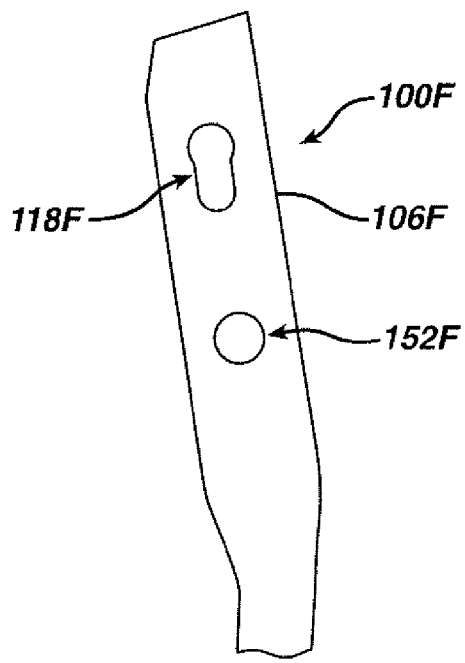
FIG. 2F is a partial plan view of another embodiment of the present invention showing a nail with a distal cross-hole in alignment with the aperture.

Referring now to FIG. 2F, another embodiment of the present invention is shown as intramedullary nail 100F. Intramedullary nail 100F is similar to the nail 100 of FIG. 2, except that the nail 100F includes a proximal cross-hole 152F that is positioned in radial alignment and distally from the aperture 100F in the proximal portion 106F of the nail 100F.

Figure 3:
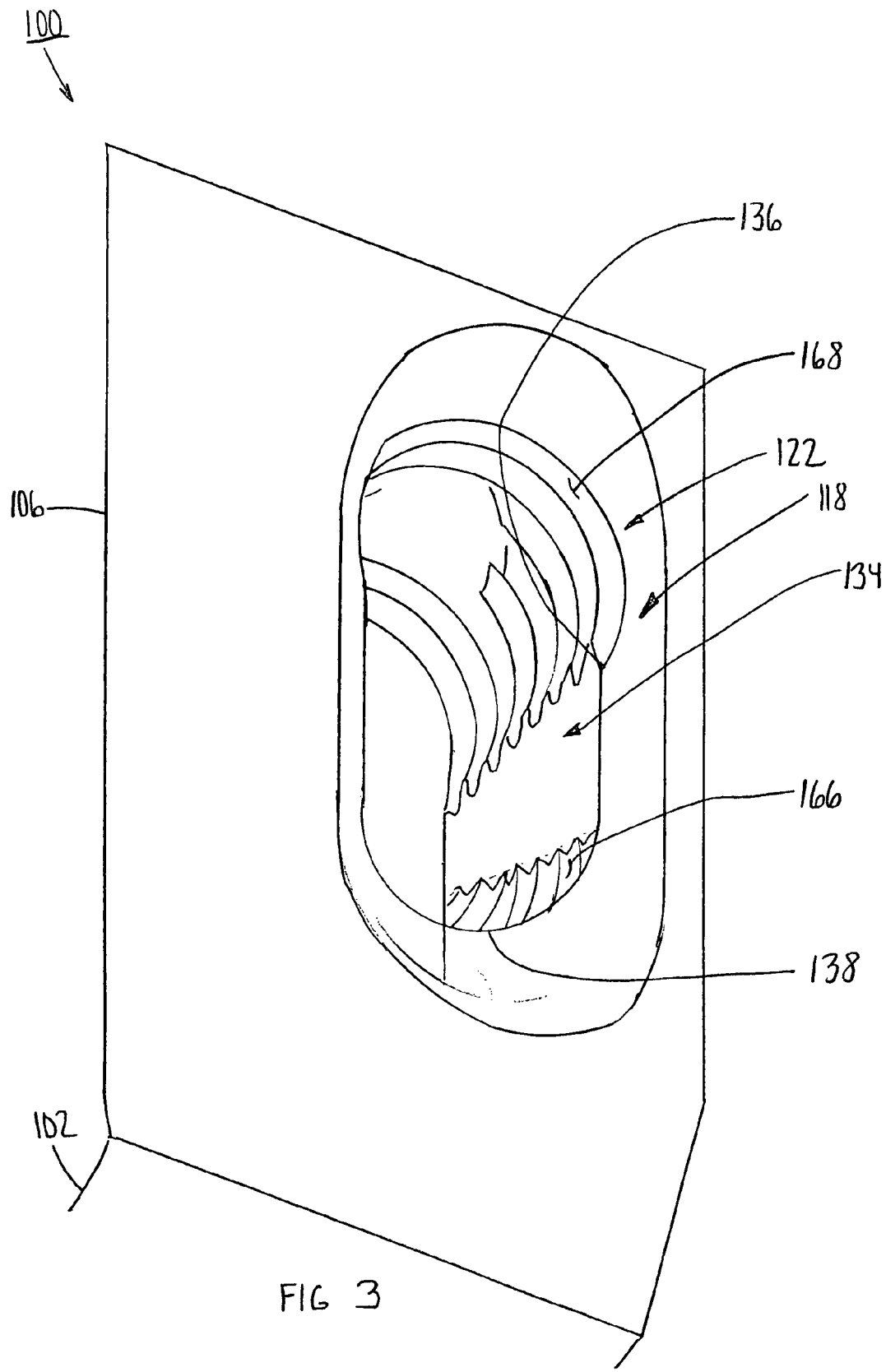
FIG. 3 is a partial perspective view of the intramedullary nail of FIG. 1 showing an aperture in the end of the nail in greater detail.

Referring now to FIG. 3, the proximal portion 106 of the body 102 of the intramedullary nail 100 is shown in greater detail. A proximal portion 106 includes the aperture 118. The aperture 118 includes the rectangular portion 134 and the enlarged portion 122. Small internal threads 166 may be formed in the distal end 138 of the rectangular portion 134 of the aperture 118. The small internal threads 166 may be adapted for cooperation with a fastener (not shown). Similarly, the enlarged portion 122 of the aperture 118 may include large internal threads 168 extending from the proximal end 136 of the rectangular portion 134. Likewise, the large internal threads 168 are adapted for cooperation with a fastener (not shown).

Figure 4:
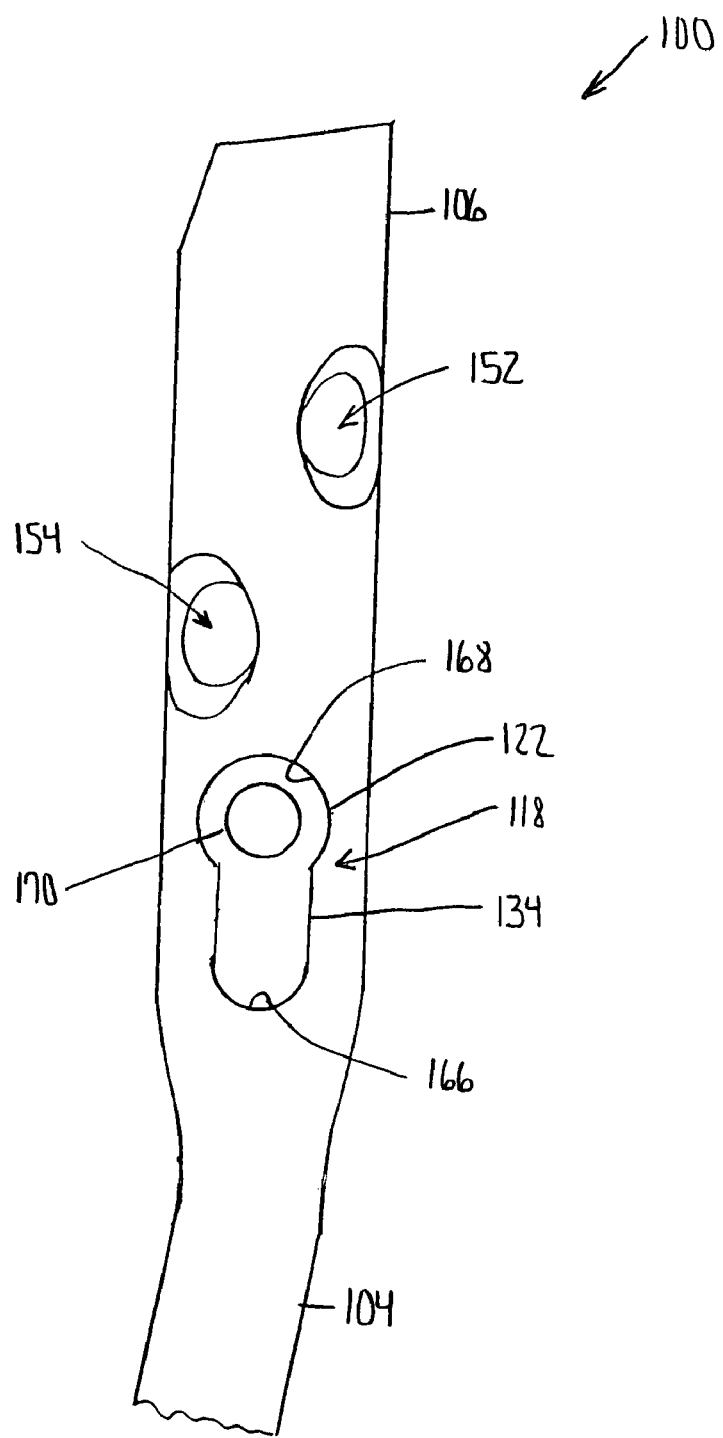
FIG. 4 is a partial plan view of the intramedullary nail of FIG. 1 showing the end of the nail with the aperture.

Referring now to FIG. 4, the proximal portion 106 of the body 102 of the nail 100 is shown in greater detail. The nail 100 as shown in FIG. 4 may cooperate with, for example, large screw or fastener 170. The large screw 170 matingly fits in the enlarged portion 122 of the aperture 118.

Referring now to FIG. 4A, the screw nail 170 is shown separate from the intramedullary nail 100. The large fastener 170 includes external threads 172, which mate with large internal threads 168 formed on the enlarged portion 122 of the aperture 118. The internal threads 168 and the external threads 172 may have any suitable size and may for example be 6 mm threads. The large fastener 170 provides for a static locking of the nail 100 to the tibia 132.

Referring now to FIG. 4B, the nail 100 is shown with the use of a medium fastener 174. The medium fastener 174 includes an unthreaded shaft portion 176 as well as a threaded shaft portion 178. The unthreaded shaft portion 176 of the fastener 174 matingly fits with minor diameter MD of the internal threads 168 of the enlarged portion 140 of the aperture 118. The medium fastener 174 and the aperture 118 combine to provide for longitudinal static locking and radial dynamic fastening application.

Referring now to FIG. 4C the nail 100 is shown with the use of a small fastener 180. The small fastener 180 includes external threads 182, which mate with small internal threads 166 of the aperture 118. The small screw 180 together with the internal threads 166 of the aperture 118 provides for a static locking application of the nail 100.

Referring now to FIG. 4D, the nail 100 is shown with a smaller fastener 184. The smaller fastener 184 includes an unthreaded shaft portion 186 as well as a threaded shaft portion 188. The unthreaded shaft portion 186 of the fastener 184 is slidably fitted into rectangular portion 134 of the aperture 118 to provide, for example, the fastener to move relative to the nail 100 from a first position 190 to a second position 192 and eventually to position 194. The smaller fastener 184 and the nail 100 combines to provide a dynamic application so that the slot, 118, permits dynamization of the long bone 132 with the use of the smaller screw 184.

Figure 5:
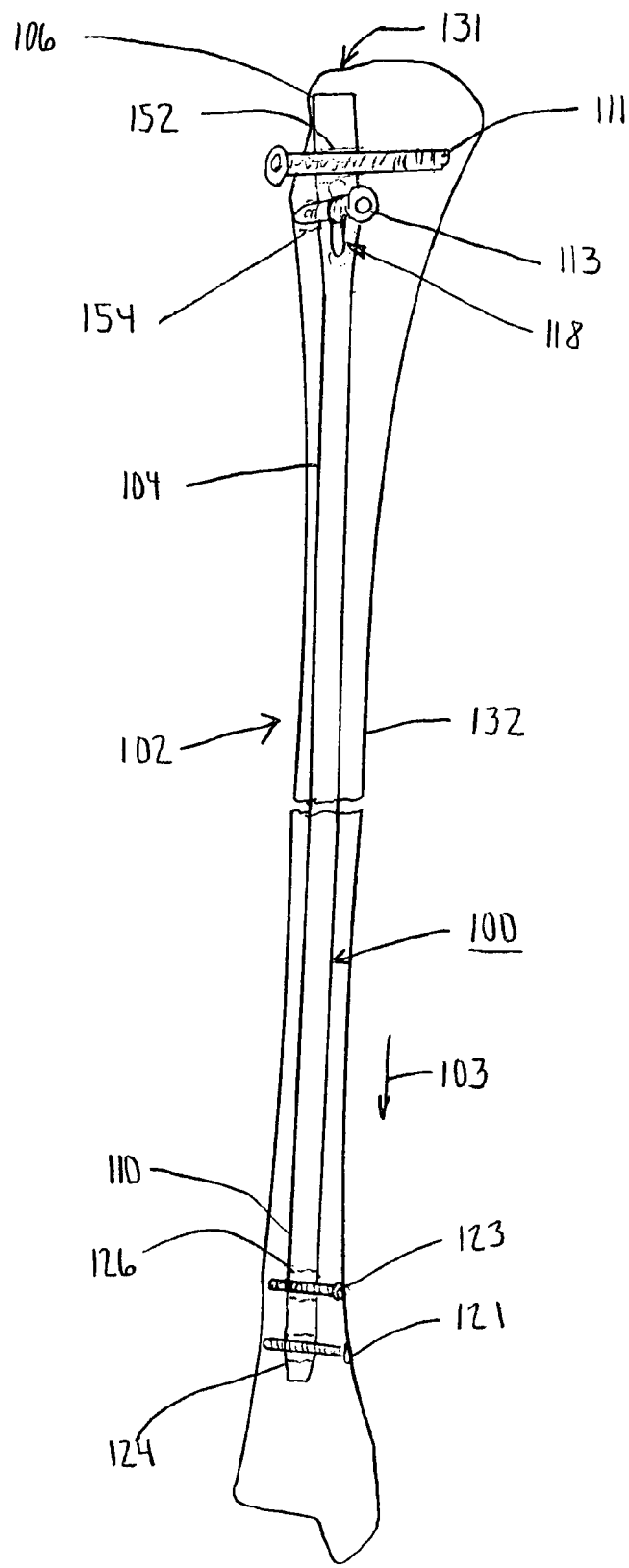
FIG. 5 is a plan view partially in cross section of the intramedullary nail of FIG. 1 showing the nail in position in a tibia.

Moving now to FIG. 5, the intramedullary nail 100 is shown in position in medullary canal 131 of long bone 132. The long bone 132 may be, as shown in FIG. 5, in the form of a tibia. The nail 100 may be inserted in the canal 131 of the tibia 132 by the positioning the distal portion 110 of the nail 100 into the proximal portion of the tibia 132 and advancing nail 100 in the direction of arrow 103. When the nail 100 may be properly secured in the canal 131 of the tibia 132.

For example, as shown in FIG. 5, first proximal fastener 111 may be positioned in first proximal hole 152. Since nail 100 is inserted in the proximal portion of the tibia 132, the proximal portion of the tibia 132 may be exposed permitting either a visual insertion of the fastener 111 into the hole 152 or the use of a fixture (not shown) to assist in aligning fastener 111 into the hole 152. It should be appreciated that a drill (not shown) may be used to drill through the cortical bone of the tibia 132 to permit the fastener 111 to be inserted into the first proximal hole 152.

First proximal fastener 111 may be any suitable, commercially available, bone screw and may be a cortical screw, for example a self-tapping cortical screw. The cortical screw may be any suitable size and may, for example, be a 3 to 6 mm screw having a length sufficient to engage the opposed cortices of the bone.

In addition to the first proximal fastener 111, the nail 110 may be used with second proximal fastener 113. The fastener 113 may be associated with, for example, the second proximal hole 154. The second proximal fastener 113 may likewise be any suitable, durable fastener and may, for example, be a self-tapping cortical screw. Such a self-tapping cortical screw may have a shank diameter of, for example, 3 to 6 mm and may have a length that is suitable to reach the opposed cortices of the tibia 132. It should be appreciated that when the intramedullary nail 100 is utilized with a small fastener positioned in the aperture 118, a dynamization of the tibia 132 is permitted due to the axial movement of the first proximal fastener 111. To encourage dynamization, a second proximal fastener 132 may not be desired.

To secure nail 100 to the tibia a fastener may be selected for use with the aperture 118. The proper fastener to be used with aperture 118 may depend on whether or not dynamization is desired for the particular application of the fracture.

For example and referring now to the aperture 118, for example, may be fastener 170, 172, 174, or fastener 176 respectively. After the appropriate fastener is positioned in the aperture 118, the distal portion 110 of the nail 100 may be secured to the long bone or tibia 132.

The first distal cross-hole fastener 121 may be associated with the first distal cross-hole 154. The first distal cross-hole fastener 121 may be in the form of a self-tapping cortical screw having a diameter of, for example, 3 to 6 mm and having a length sufficient to engage the opposed cortices of the tibia 132.

The nail 100 may be secured to the tibia 132 in the distal portion 110 of the nail 100 by use of, in addition to first fastener 121, a second distal cross-hole fastener 123 which may be associated with the second drill cross-hole 126. The second drill cross-hole fastener 123 may, as with fastener 121, be in the form of a self-tapping cortical screw having a diameter of, for example, 3 to 6 mm, and a length sufficient to reach the opposed cortices of the tibia 132. For example, the first fastener 121 and the second fastener 123 may be a 4½ mm cortical screw. The first proximal fastener 111 and the second proximal fastener 113 may be in the form of 5½ mm diameter self-tapping cortical screws.

The first and second distal cross-hole fasteners 121 and 123 may be positioned by using the radiolucent drill guide system (not shown) or by using a standard free hand technique.

Figure 6:
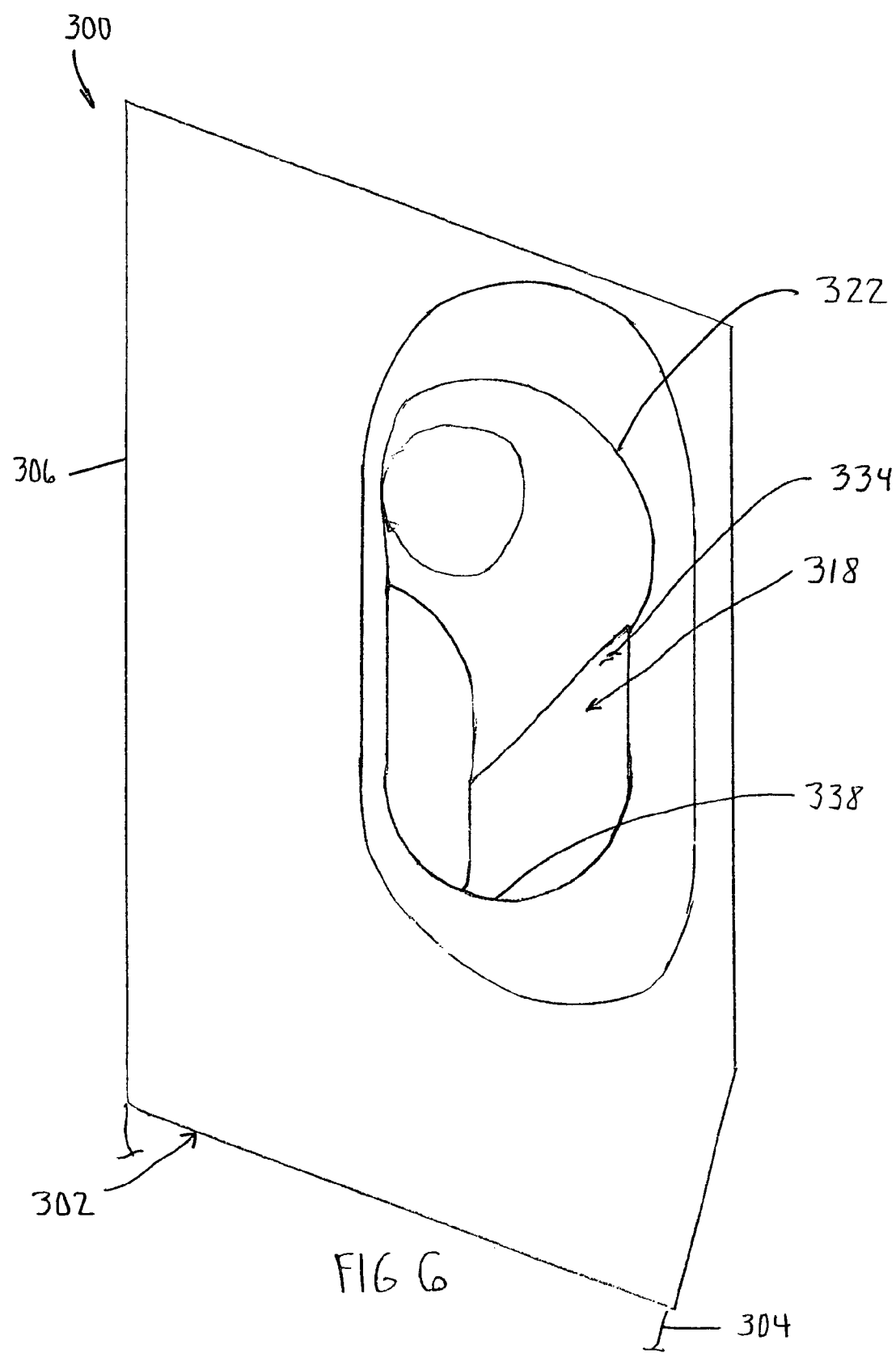
FIG. 6 is a partial perspective an intramedullary nail with an aperture in the end of the nail having no threads in accordance with another embodiment of the present invention.

Referring now to FIG. 6, another embodiment of the present invention is shown as intramedullary nail 300. Intramedullary nail 300 is similar to the nail 100 of FIGS. 1-5 except that the intramedullary nail 300 includes an aperture 318 that is different than the aperture 118 of the nail 100. For example, intramedullary nail 300 includes a body 302 similar to the body 102 of the nail. The body 302 includes a center portion 304 from which a proximal portion 306 extends.

The proximal portion 306 defines aperture 318 there through. The aperture 318 unlike the aperture 118 of the nail 100 does not include internal threads. For example, the aperture 318 includes a central section 324 and enlarged section 322 extending proximally from the central section 334.

The central section 334 includes a distal end 338, which is rectangular but does not include internal threads. Fasteners (not shown) in the form of, for example, cortical screws as shown in FIGS. 1-4 may be associated with the distal end 338 of the aperture 318 and associated with the enlarged section 322 of aperture 318. The fasteners may be used in conjunction with aperture 318 to limit axial motion of the nail, but to permit radial movement of nail within the medullary canal of the tibia.

Figure 7:
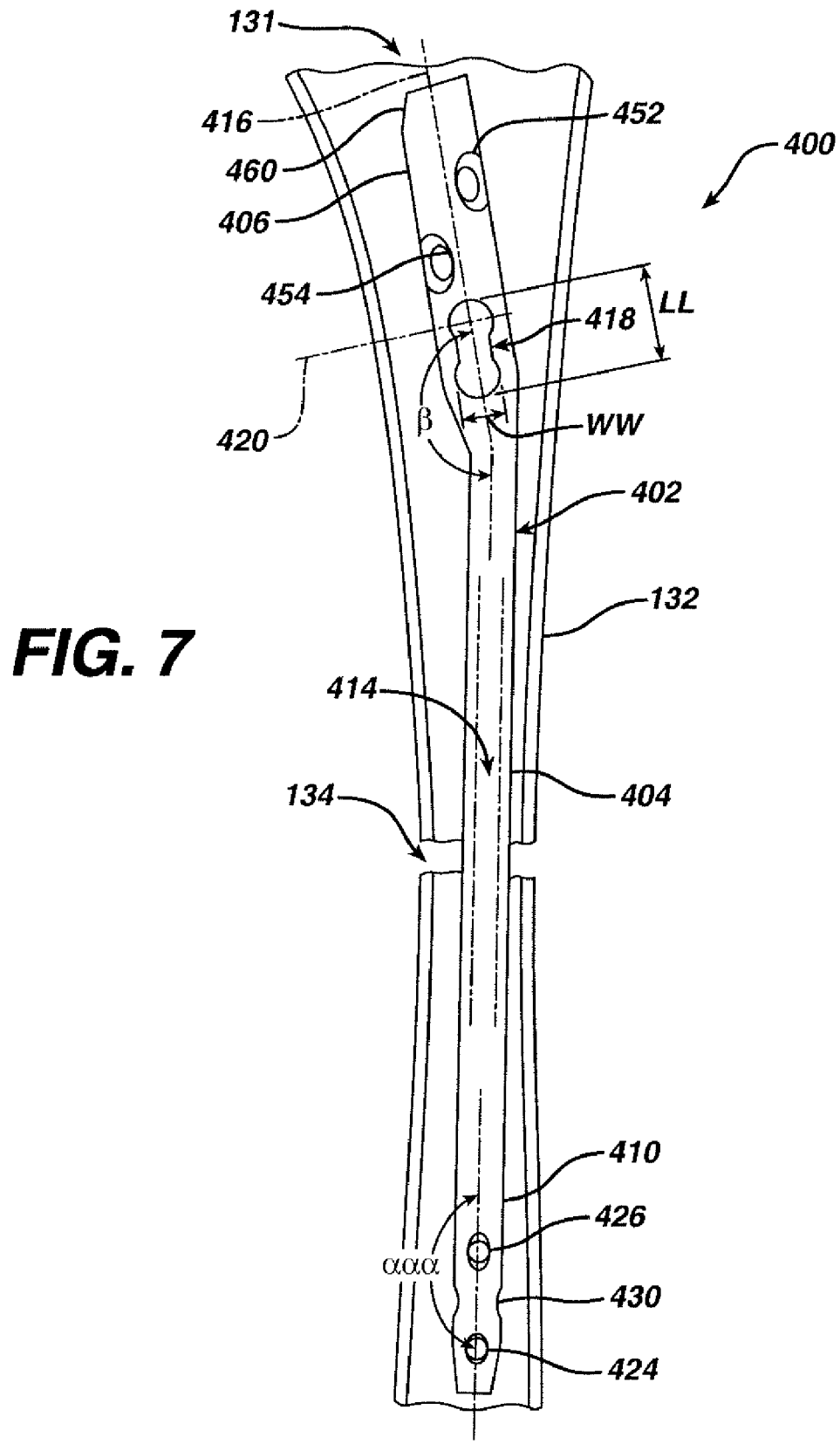
FIG. 7 is a plan view of an intramedullary nail with an aperture in the end of the nail having two opposed cylindrical areas in accordance with yet another embodiment of the present invention.

Referring now to FIG. 7, another embodiment of the present invention is shown as intramedullary nail 400. Intramedullary nail 400 like the intramedullary 100 of FIGS. 1-5 and intramedullary 300 of FIG. 6 is for insertion into the medullary canal 131 of long bone 132 to repair a fractured long bone.

The nail 400 may be used with any long bone, for example, a femur, tibia, humerus, ulna, or any other long bone in the body. As shown in FIG. 7, the intramedullary nail 400 is shown in use in a tibia 132.

While the intramedullary nail 400 may have any suitable shape that is capable of fitting into the canal 131 of tibia 132, for example, the intramedullary nail size and shape may be generally similar to that of the intramedullary nail 100 of FIGS. 1-5.

For example, as shown in FIG. 7 intramedullary nail 400 includes a body 402. The body 402 is designed to fit into the canal 131 and is generally elongated. The body 402, to minimize weight and to maximize strength, may be hollow or cannulated and may include a central opening or cannula 414.

Since the long bone, for example, the tibia 132 is not entirely straight the body 402 may have a similar non-straight shape. For example, the body 402 may include a central portion 404 along with a distal portion 410 extending from the central portion 404 at an angle, for example ααα. Further the body 402 may include a proximal portion 406 extending at, for example β from the central portion 404.

The proximal portion 406, may define a longitudinal axis 416. According to the present invention, an opening or aperture 418 is formed in the body 402. For example, aperture 418 may be located in the proximal portion 406 of the nail 400. The aperture 418 includes a length LL, which is larger then the width WW of the aperture 418. In other words, the aperture 418 extents longer along longitudinal axis 416 then in a transverse axis for 420 normal to the longitudinal axis 416.

The distal portion of 410 of nail 400 may be secured or positioned in place within the canal 131 with the use of openings or cross-holes located in the distal portion 410 of the nail 400. For example, the distal portion 410 of the nail 400 may include a first distal cross-hole 424. In addition to the first distal cross-hole 424, a second distal cross-hole 426 may be positioned spaced from the first distal cross-hole 424. Additionally, a groove or recess 430 may be formed in the body 402 of the distal portion 410 of nail 400.

While the nail of the present invention may include merely the aperture 418 in the proximal portion 406 of the nail 400, the nail 400 may further include a first proximal cross-hole 452 and a spaced apart second proximal cross-hole 454. The proximal portion 406 of the nail 400 may further include features to accommodate soft tissue adjacent the proximal portion 406 of the nail 400. For example, the proximal portion 406 may include a flat 460 to permit ligaments or tendons from making contact with the nail 400.

The proximal cross-holes, for example first proximal cross-hole 452 and the second proximal cross-hole 454, may be positioned anyplace within the proximal portion 406 with the nail 400. For example, as is shown in FIG. 7, the first proximal hole 452 may be positioned proximally and to the right of the aperture 418. The second proximal hole 454 may be positioned to the left of the aperture 418 and between the first proximal hole 452 and the aperture 418.

Figure 7A:
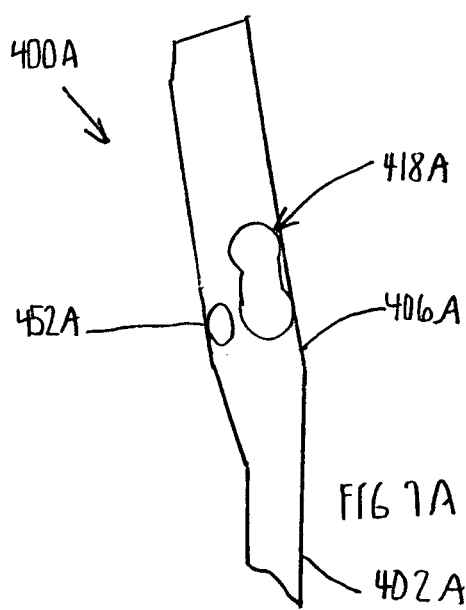
FIG. 7A is a partial plan view of another embodiment of the present invention showing a nail with a distal cross-hole.

Referring now to FIG. 7A, a nail 400 is shown in which the proximal portion 406 of the body 402 of the nail 400 utilizes a solidity proximal cross-hole 452A. The proximal cross-hole 452A is positioned and aligned with the distal portion of the aperture 418A.

Figure 7B:
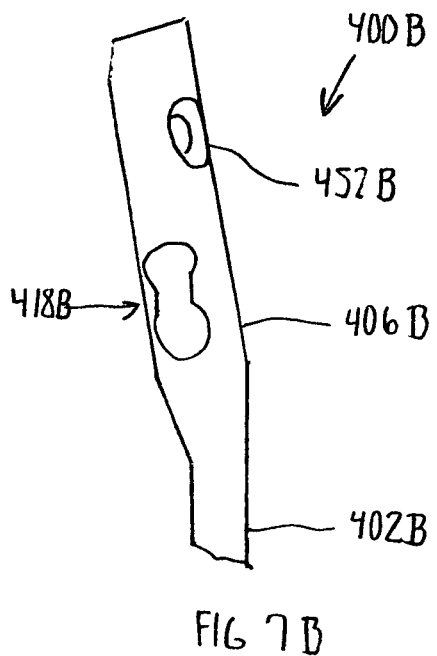
FIG. 7B is a partial plan view of another embodiment of the present invention showing a nail with a proximal cross-hole.

Referring now to FIG. 7B, another embodiment to the present invention is shown as intramedullary nail 400B. Intramedullary nail 400B is similar to the intramedullary nail 400 of FIG. 7 except that the nail 400B includes a solitary first proximal cross-hole 452B, which is positioned in a location different than that of the nail 400A of FIG. 7A. The nail 400B includes a first proximal cross-hole 452B that is positioned proximally with respect to the aperture 418B on the proximal portion 406B of the body 402B of the nail 400B.

Figure 7C:
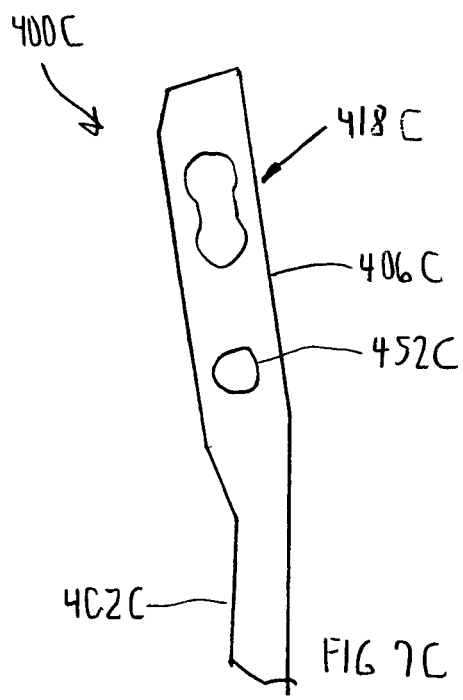
FIG. 7C is a partial plan view of another embodiment of the present invention showing a nail with a distal cross-hole in alignment with the aperture.

Referring now to FIG. 7C, another embodiment of the present invention is shown as intramedullary nail 400C. The nail 400C includes a solitary proximal cross-hole 452C that is positioned distally and is in alignment with the aperture 418C. The aperture 418C and the proximal hole 452C are both positioned in proximal position 406C of the body 402C of the nail 400C.

Figure 7D:
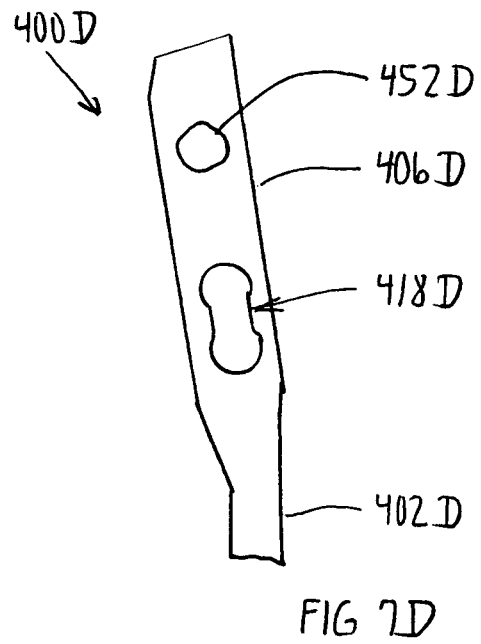
FIG. 7D is a partial plan view of another embodiment of the present invention showing a nail with a proximal cross-hole in alignment with the aperture.

Referring now to FIG. 7D, another embodiment of the current invention is shown as intramedullary nail 400D. The nail 400D is similar to the nail 400C of FIG. 7C except that the proximal cross-hole 452D is positioned proximally and in alignment with the aperture 418D in the proximal portion 406D of body 402D of the nail 400D.

Figure 8:
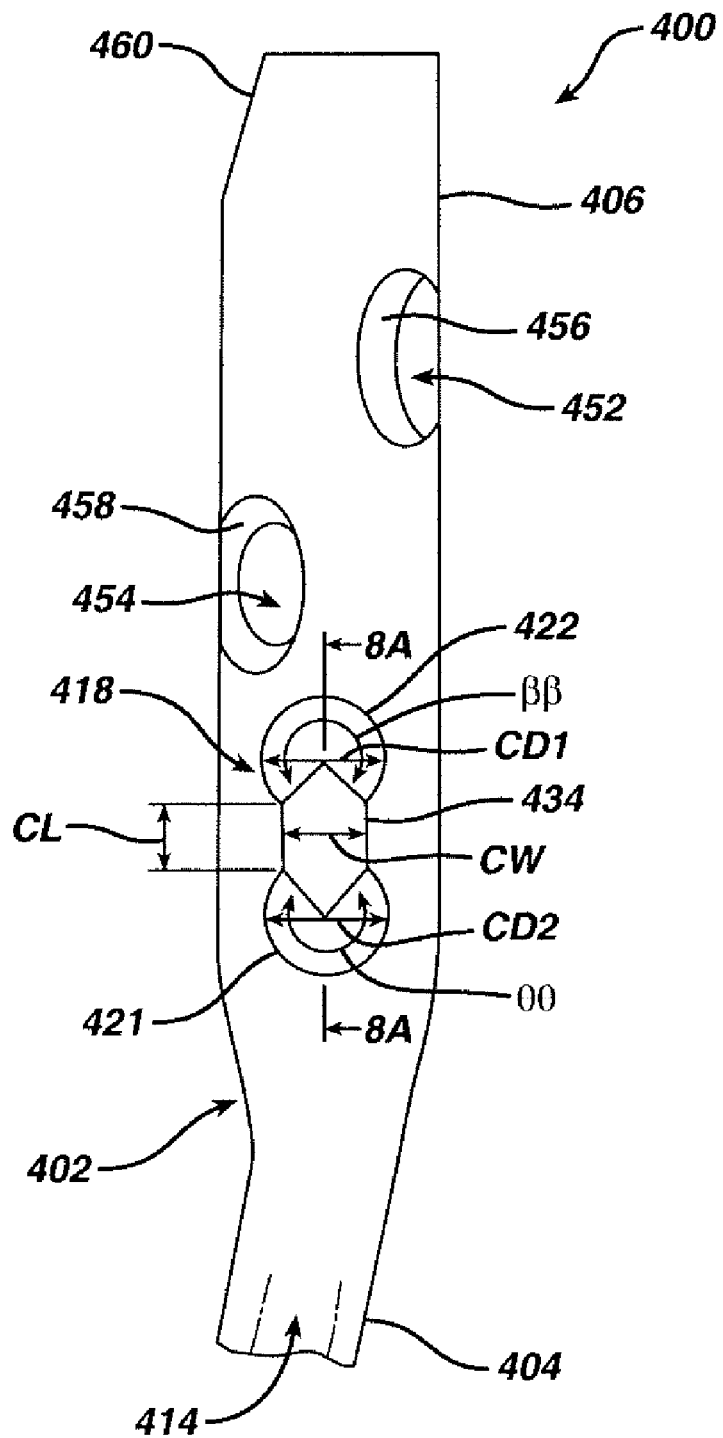
FIG. 8 is an enlarged partial plan view of the intramedullary nail of FIG. 7 showing an end of the nail in greater detail.

Referring now to FIG. 8, the nail 400 of FIG. 7 is shown in greater detail. The aperture 418 may include a center section 434. The center section 434 may have a generally a rectangular cross section.

The aperture 418 may further include an enlarged section 422. For example, a cylindrically shaped proximal enlarged section 422 may be positioned, as shown in FIG. 8, proximally with respect to the center section 434.

The aperture of the intramedullary nail 400 may further define a second enlarged section 421. The second enlarged section 421 may have a generally cylindrical shape and may be positioned distally from central section 434.

The aperture 418 may have any suitable shape, and may as shown in FIG. 8 include the central section 434 having a generally rectangular shape defining width CW. Cylindrical sections for example, proximal cylindrical section 422 and distal cylindrical section 421 may have generally cylindrical shape, which may be defined by a diameter CD1 and CD2, respectively. The diameters CD1 and CD2 may be generally the same and may be larger than the width CW of the central section 434.

The first cylindrical section 422 may be defined by an included angle ββ and the second cylindrical section 421 may be defined as an angle θθ. The central section 434 may have a length, for example, CL.

While the nail 400 of the present invention may include solitary aperture 418 it should be appreciated that nail 400 can further include first proximal cross-hole 452. To assist in inserting a fastener into the cross-hole 452, a first chamfer 456 may be positioned concentric to the first cross-hole 452.

It should be appreciated in addition to the first proximal cross-hole 452 a second proximal cross-hole 454 may be positioned in the nail 400. The second proximal cross-hole 454 may also include a second chamfer 458 positioned concentric to the second cross-hole.

Figure 8A:
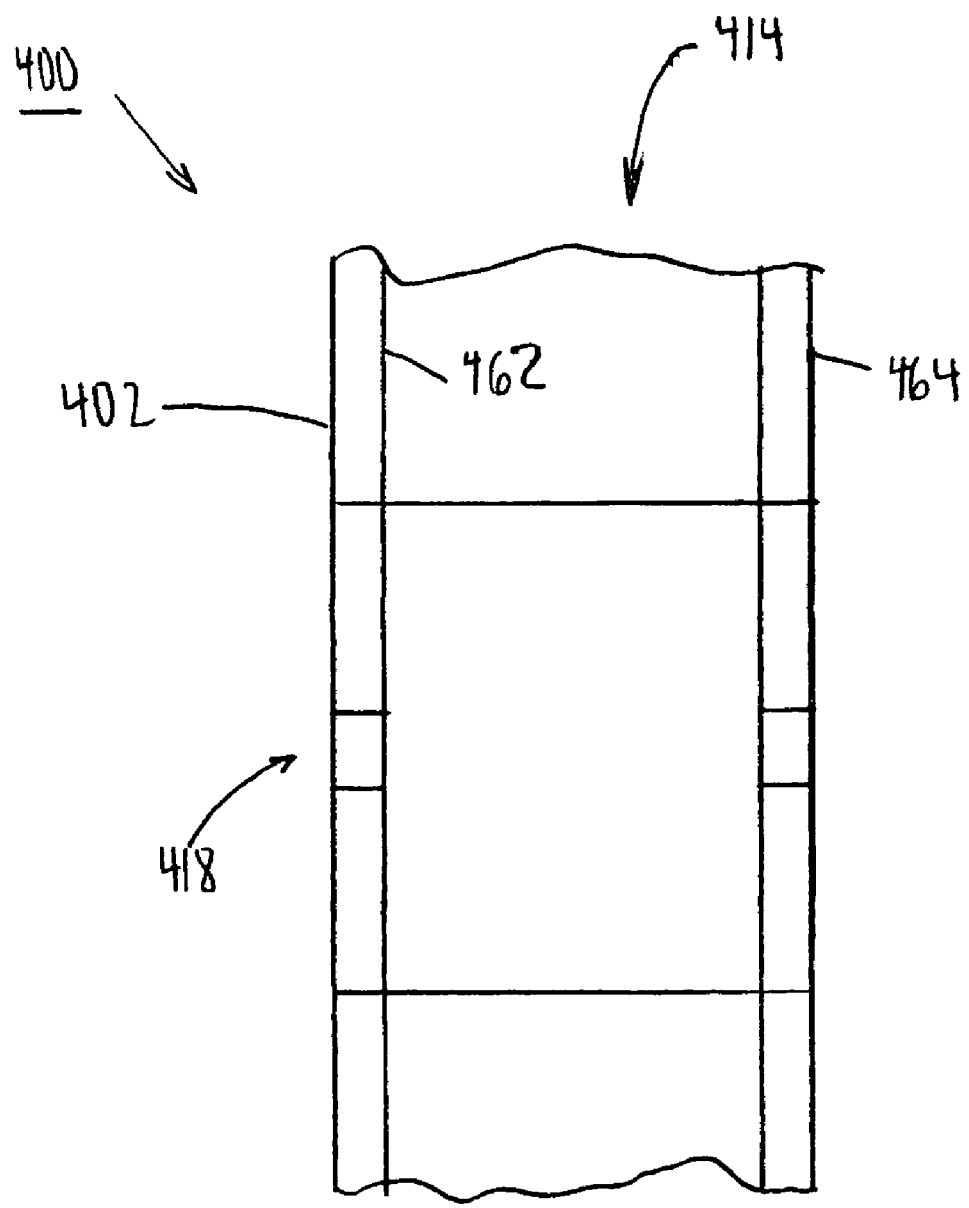
FIG. 8A is partial cross sectional view of FIG. 2 along the lines 8A8A in the direction of the arrows.

Referring now to FIG. 8A, the aperture 418 formed in the body 402 of the nail 400 passes through first wall 464 formed the body the 402 to form cannula 414 as well as second wall 464 of the body 402.

Figure 9:
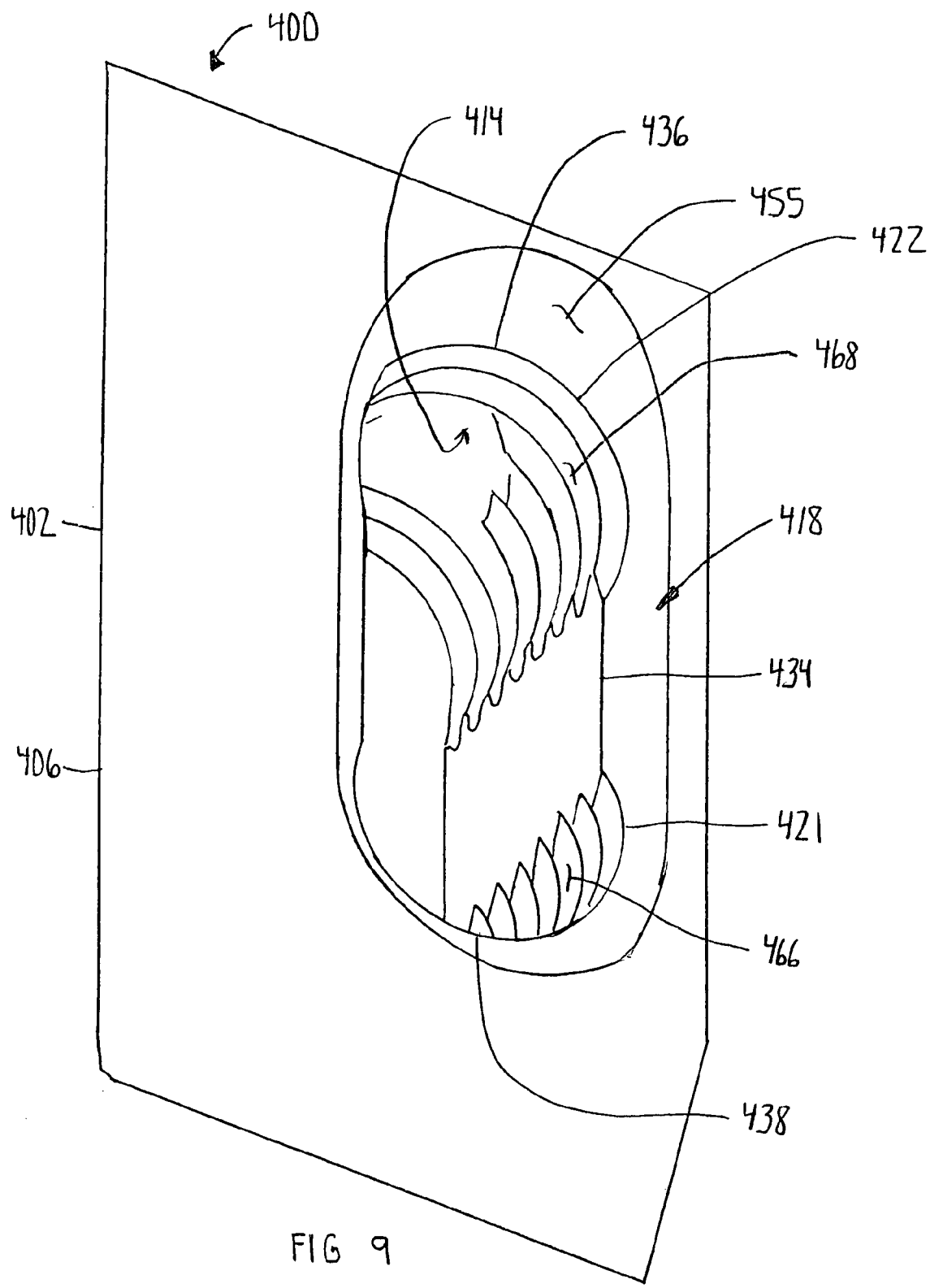
FIG. 9 is a partial perspective view of the intramedullary nail of FIG. 7 showing an aperture in the end of the nail in greater detail.

Referring now to FIG. 9, the aperture 418 is shown in greater detail. The aperture 418 of the nail 400 may include a feature in the form of, for example, a chamfer 455 for guiding a fastener into the aperture 418. The aperture 418 may further include a distal internal thread 466 formed in distal end 438 of the second cylindrical section 421 of the aperture 418. The distal internal thread 466 is utilized to cooperate with a fastener.

The aperture 418 of the nail 400 may further include a proximal internal thread 468 formed in the first cylindrical section 422 of the aperture 418. The internal threads 468 are used to cooperate with a fastener (not shown).

Figure 10:
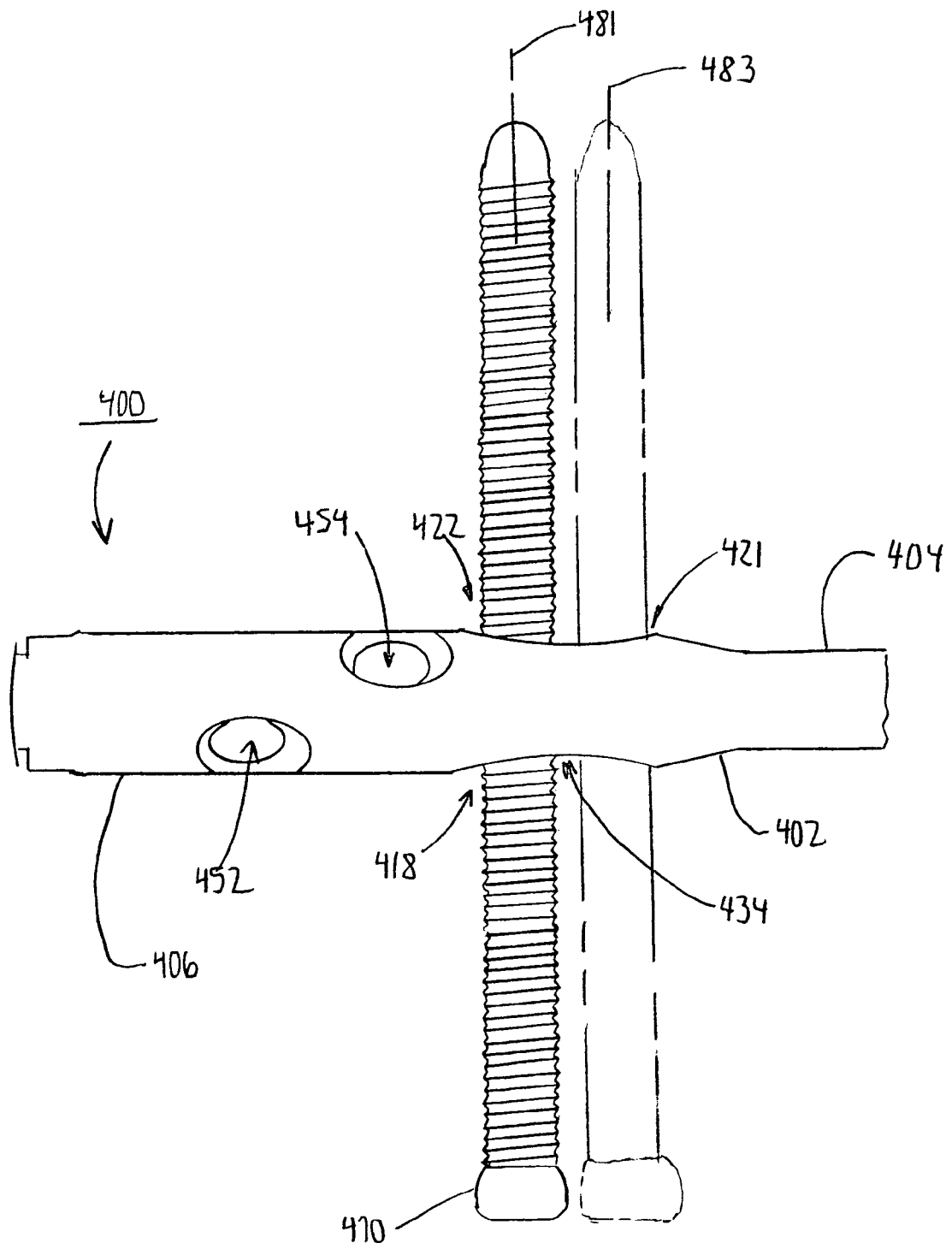
FIG. 10 is a partial plan view of the intramedullary nail of FIG. 7 showing a fully threaded fastener positioned in the aperture.

Referring now to FIG. 10, a fastener 470 is shown in cooperation with the body 402 with the nail 400. The cylindrical sections 422 and 421 of the body 402 are adapted to matingly fit with the fastener 480. For example as is shown in FIG. 10, the fastener 480 may cooperate with the proximal section 422 of the aperture 418 of the nail 400. In such cooperation, the fastener 480 defines a first centerline position 481. Alternatively, the fastener 480 may be positioned in a second centerline position 483, as is shown in phantom. When in the second position 483, the fastener 480 cooperates with the distal section 421 of the aperture 418 of the nail 400.

Figure 11:
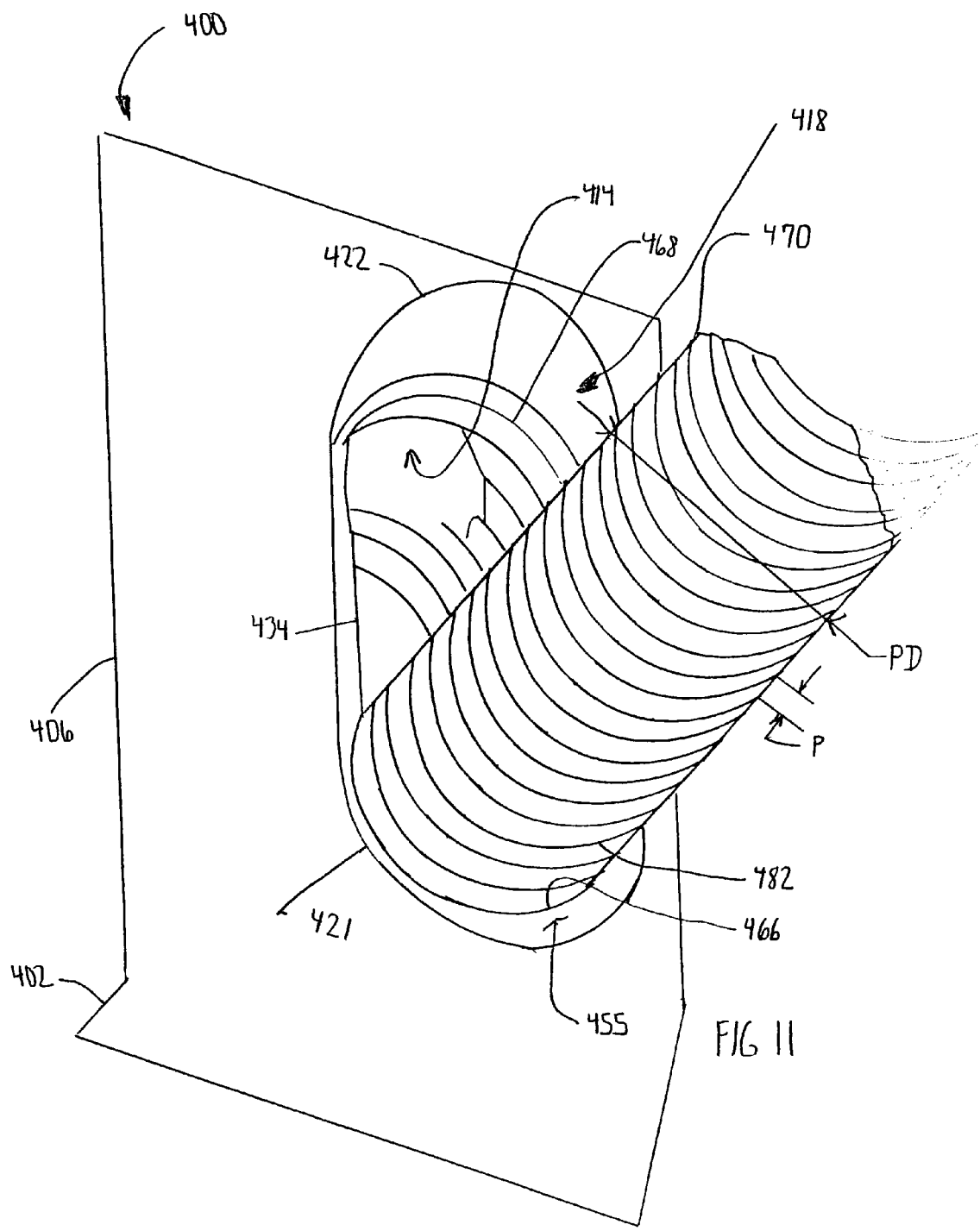
FIG. 11 is a partial perspective view of the intramedullary nail and fastener assembly of FIG. 10 showing in greater detail the aperture and the fastener in the distal end of the aperture.

Referring now to FIG. 11, the fastener 470 and the aperture 418 are shown in greater detail. As is shown in FIG. 11, the fastener 470 is shown engaged with the large distal section 421 of the aperture 418. As shown in FIG. 11, the fastener 470 includes external threads 482, which preferably mates with the internal threads 466 located on the enlarged distal section 421.

The fastener 480 may be any suitable fastener for use with the bone.

The fastener 470 may be a cancellous or a cortical fastener or screw. For example, the fastener 470 may be a locking cortical screw, for example a fully threaded cortical screw having a pitch diameter PD as well as a pitch P. For example, the cortical screw 470 may have a pitch diameter PD, for example, of 6.0 mm and a, for example, pitch P of 2 mm. With the cooperation with the fastener 470 the enlarged distal section 421 may have the internal threads 466 having a pitch PD, and a pitch P generally the same as the fastener 470.

Figure 12:
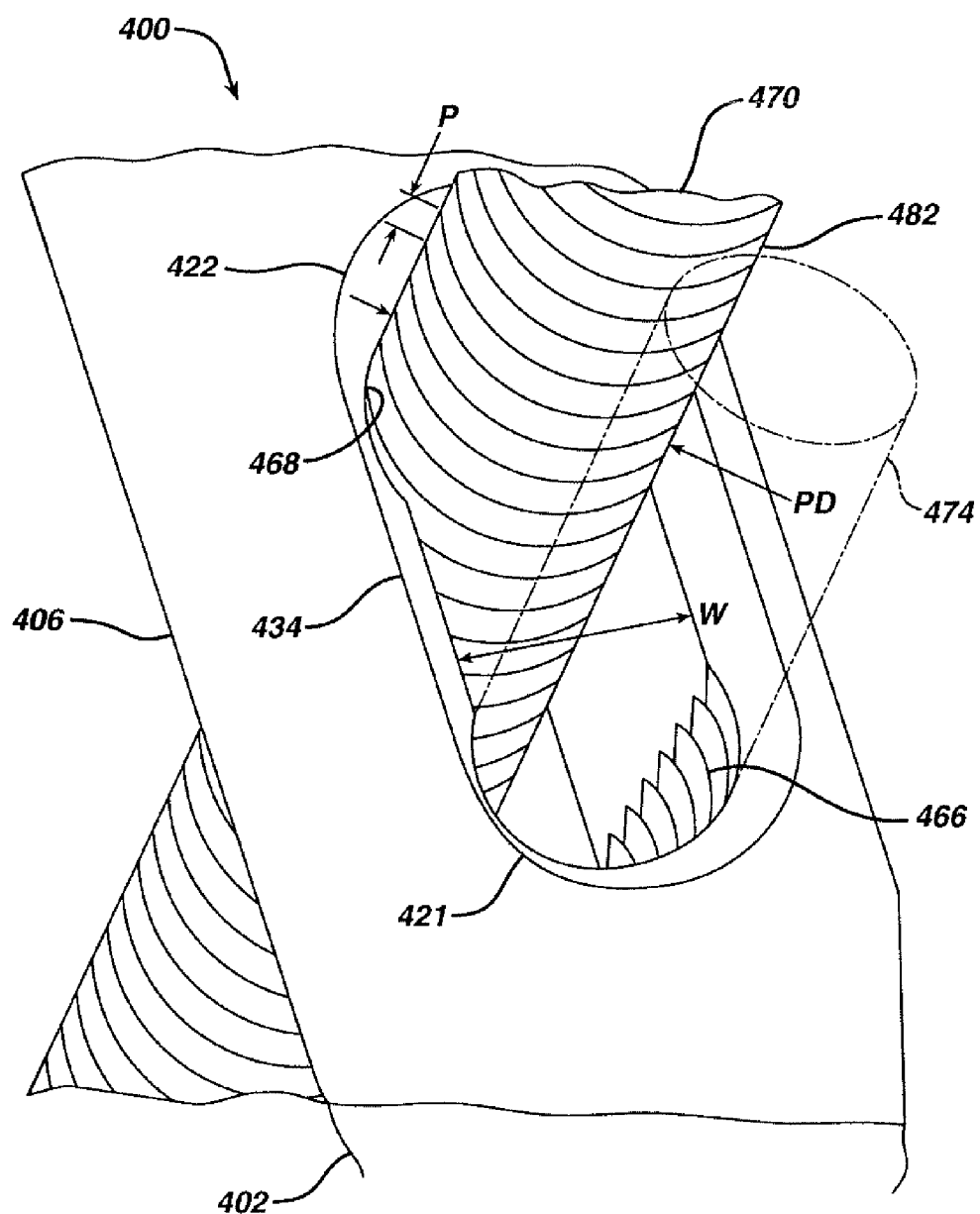
FIG. 12 is a partial perspective view of the intramedullary nail and fastener assembly of FIG. 10 showing in greater detail the aperture and the fastener in the proximal end of the aperture.

Referring now to FIG. 12, the fastener 470 is shown in position with the enlarged proximal section 422 of the aperture 418. It should be appreciated that the enlarged proximal section 422 preferably includes internal threads 468 that mate with the external threads 482 of the fastener 470. The internal threads 468 may have a pitch diameter PD and a pitch P similar to that of the fastener 470 to provide engagement with the fastener 470.

The aperture 418 may include the central section 434 having the width W, which is less then the pitch diameter PD of the enlarged distal section 421 and the enlarged proximal section 421. For example, the central section 434 may have a width w of, for example, 4.5 mm.

Figure 12A:
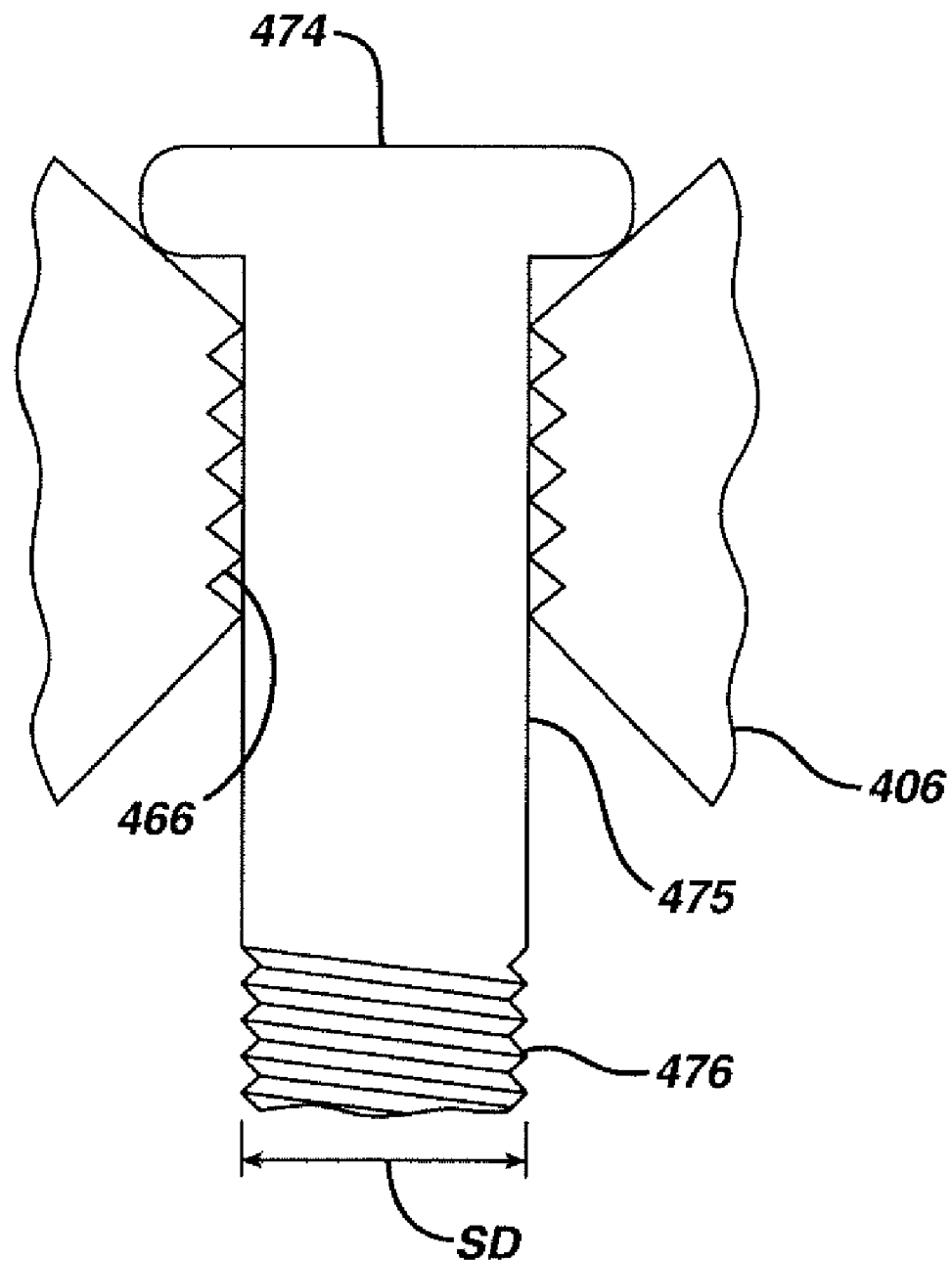
FIG. 12A is a partial plan view, partially in cross section of the intramedullary nail of FIG. 7 showing a partially threaded fastener positioned in the aperture.

Referring now to FIGS. 12 and 12A, a fastener 474 is shown in position in phantom in FIG. 12 in position in distal section 421 of the aperture 418. The fastener 474 is slidably fitted to internal threads 466 of distal section at shank portion 475 of fastener 474. The fastener may prohibit axial motion while permitting transverse motion. The fastener 474 may have an unthreaded shank portion 475 and a threaded shank portion 476. The fastener 474 may be a cortical screw, for example a partially threaded cortical screw having a shank diameter SD of, for example, 5.75 mm to mate with minor diameter of internal threads 466 and 468.

Figure 13:
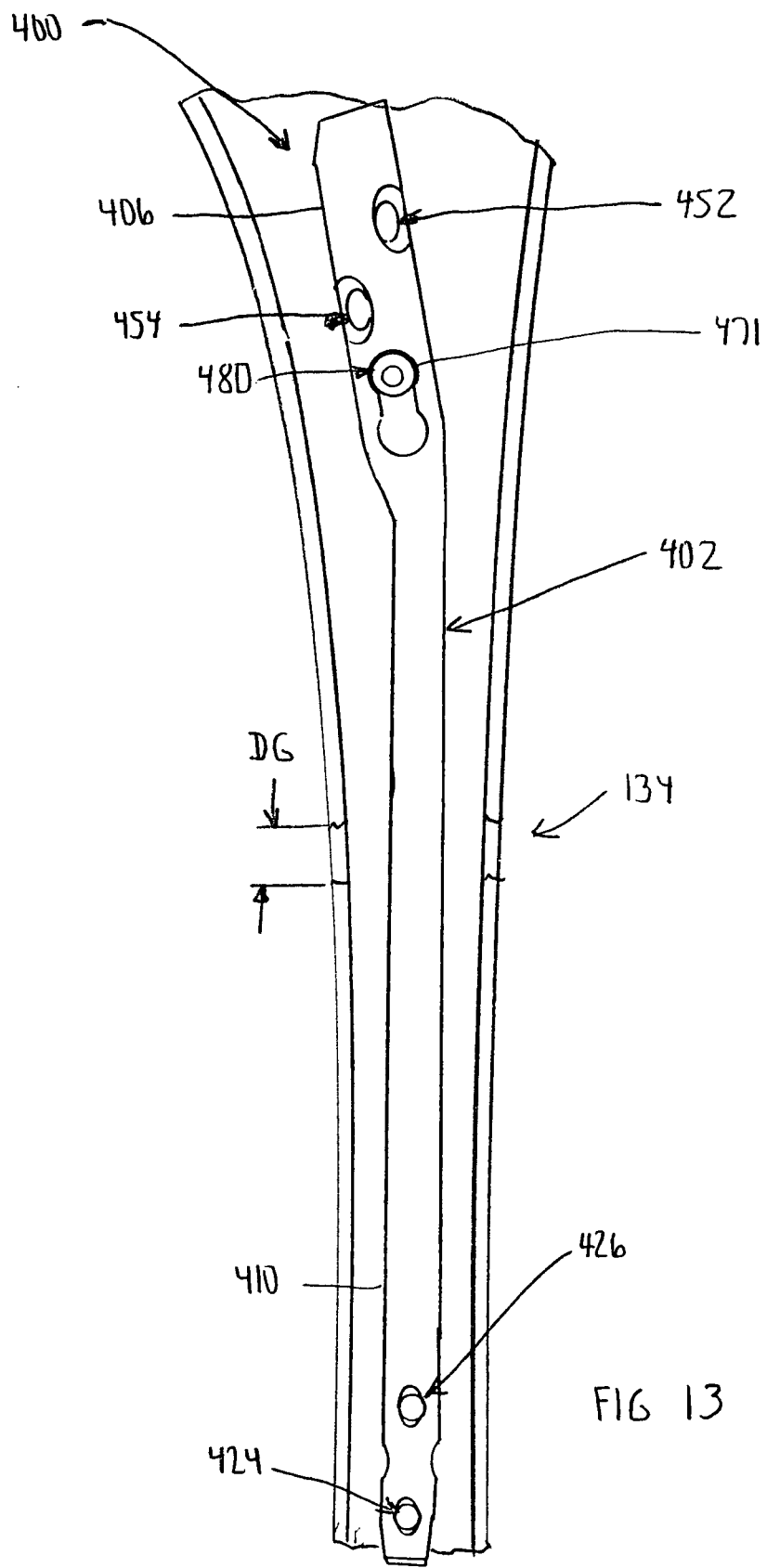
FIG. 13 is a plan view of the intramedullary nail of FIG. 7 showing a threaded fastener positioned loosely in the aperture to permit limited dynamization.

Referring now to FIG. 13, intramedullary nail of the present invention is shown for use in applications with limited dynamization. To promote healing of the fracture site 134 limited motion of the tibia may be desired to provide compression to the fracture site 134, and to promote healing at the fracture site. Dynamization can occur by permitting motion under load of the fastener with the respect to the nail 400.

Figure 13A:
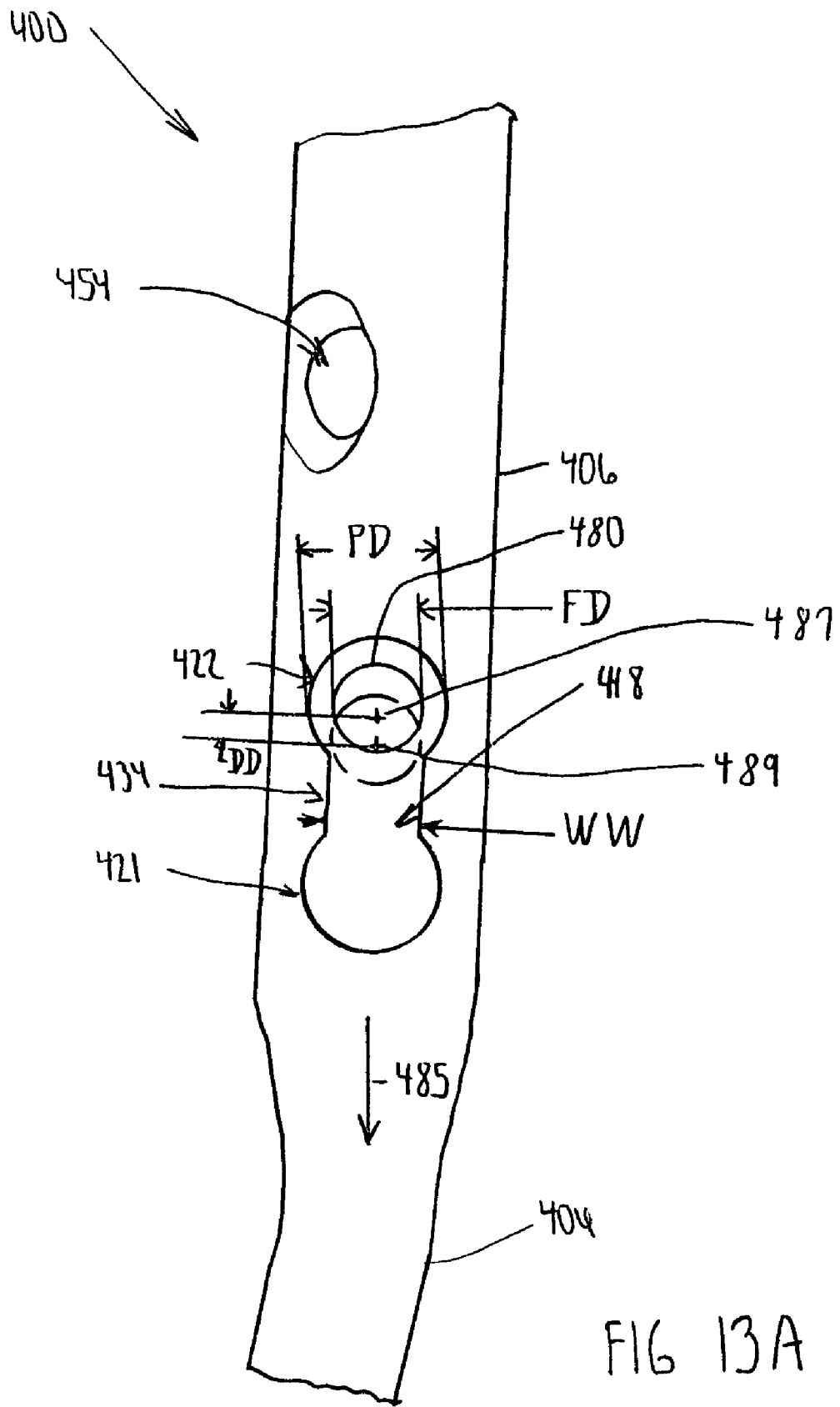
FIG. 13A is a partial plan view of FIG. 13.

As shown in FIGS. 13 and 13A, the intramedullary nail 400 may be used with a fastener 480 that provides clearance between the aperture 418 and the fastener. Such a fastener may be fastener 480 of FIG. 13. The fastener 480 has a fastener diameter FD that is smaller then diameter PD of the large proximal portion 422 and the enlarged distal section 421. The diameter FD of the fastener 480 is also larger then the width WW of the central section 434 of the aperture 418.

If the fastener 480 is positioned centrally in, for example, the enlarged proximal section 422 of the aperture 418 of the nail 400, the fastener 480 may migrate under load in the direction of arrow 485 from first center line 487 to second center line 489. Such migration or motion of the fastener 480 may provide for a dynamization distance DD.

Figure 14:
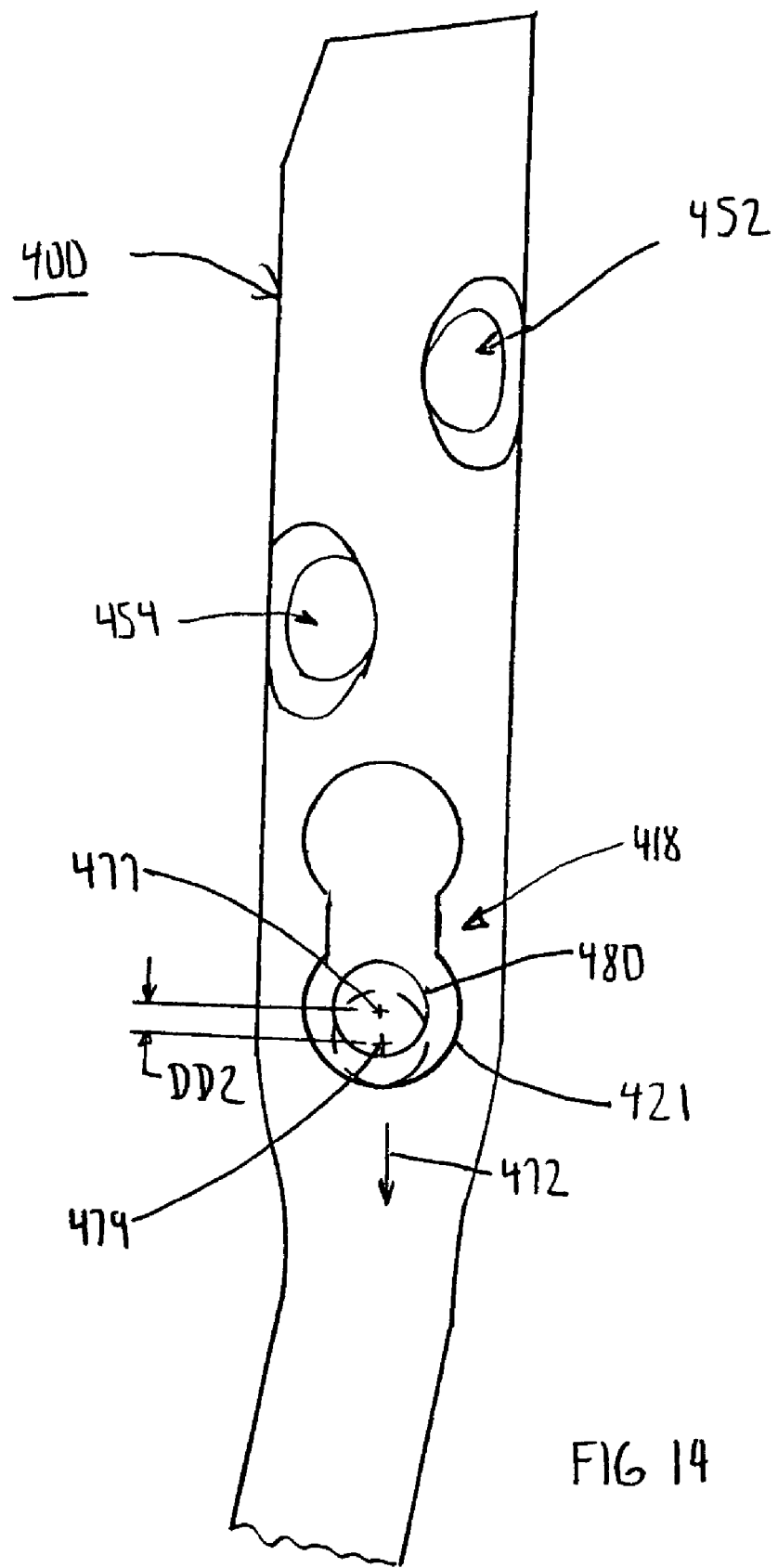
FIG. 14 is a partial plan view of the intramedullary nail and fastener assembly of FIG.13.

Referring now to FIG. 14, fastener 480 may be centrally positioned in the enlarged distal section 421 at first centerline 477. As the fastener 480 moves under load in the direction of arrow 472 from the first centerline 477 to second centerline 479, the nail 400 and the fastener 480 may provide for a limited dynamization distance of DD2.

It should be appreciated since the fastener 480 does not engage with the threads 466 or 468 on nail 400, the fastener 480 may be fully threaded or partially threaded. It should be appreciated the fastener has a suitable length for engagement with, for example, the opposed cortices of the tibia.

Figure 15:
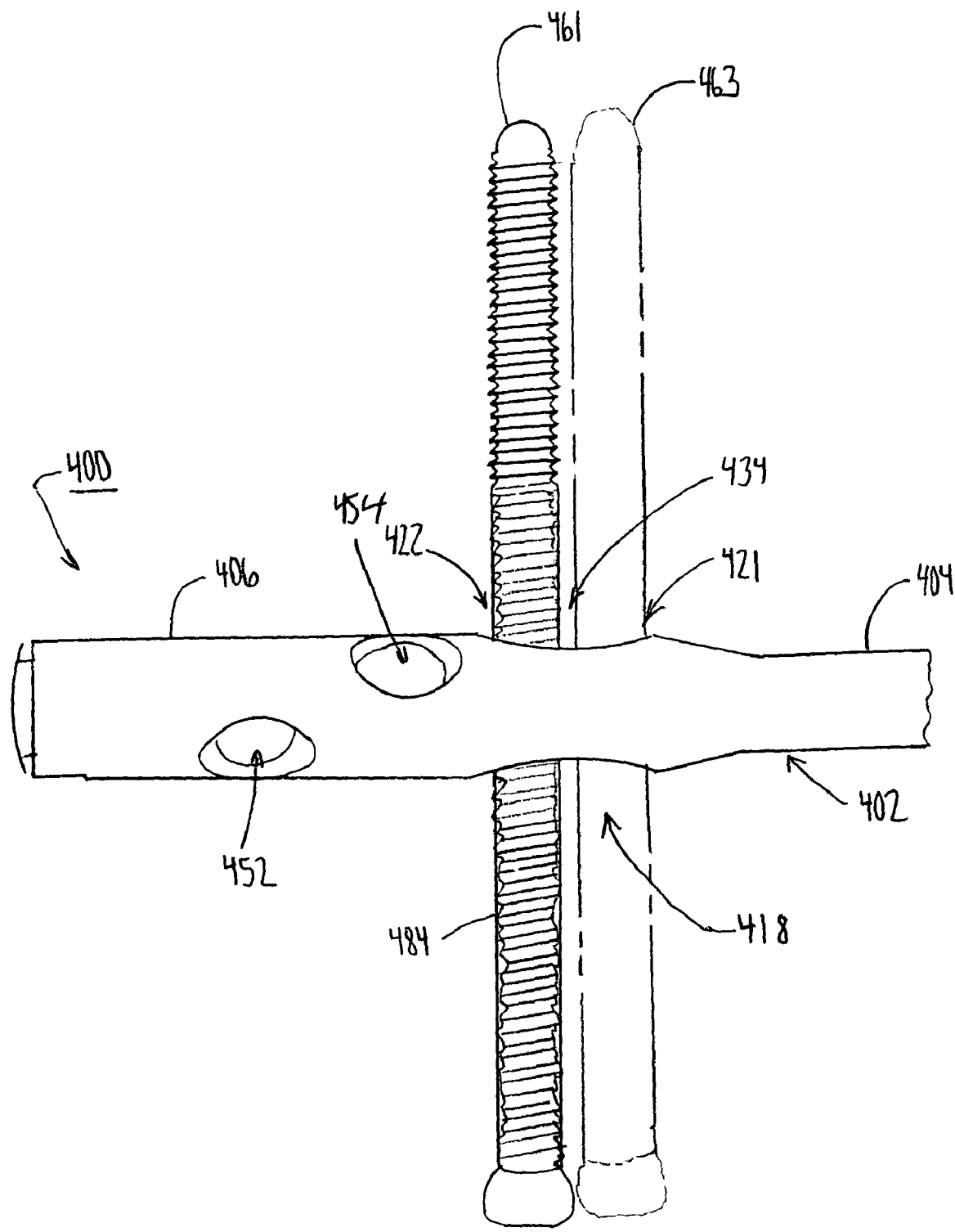
FIG. 15 is a partial plan view of the intramedullary nail of FIG. 7 showing a smaller threaded fastener positioned in the aperture to permit full dynamization along the length of the aperture.
Figure 16:
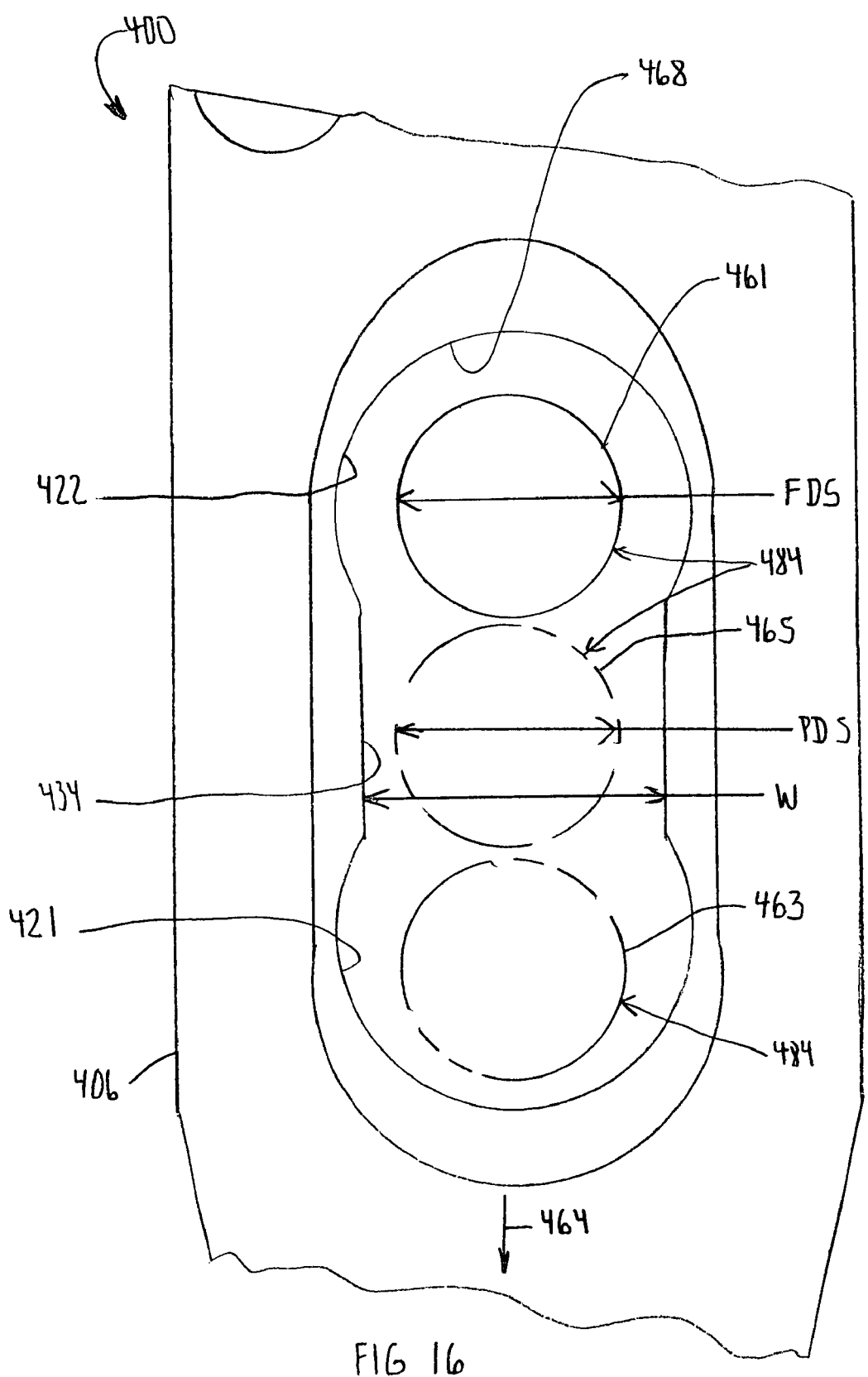
FIG. 16 is a partial perspective view of the intramedullary nail and fastener assembly of FIG. 15 showing in greater detail the aperture and the fastener in the aperture.

Referring now to FIGS. 15 and 16, the nail 400 of the present invention is shown for use with full dynamization. A fastener, for example fastener 484, may be fitted in the aperture 418 of the nail 400 to provide for motion substantially along the length of aperture 418. The fastener 484 may be any fastener capable of providing motion within the aperture 418 from a first position 461 as shown in solid to a second position 463 as shown in phantom.

The fastener 484 may be a cortical or cancellous screw and may have any length capable of attachment to the bone for example, the tibia. The cortical screw 484 may be a fully threaded or a partially threaded screw. For example, as shown in FIG. 15 the screw 484 is in the form of a cortical screw having a fully threaded configuration. Cortical screw 484 may be self drilling and or self-tapping.

Referring now to FIG. 16, the fastener 484 is shown in solid in first position 461 as well as in phantom in final position 463 and intermediate position 465. To provide for maximum dynamization, the fastener 484 is installed in first position 461 and allowed to migrate through the dynamization process from first position 461 in the direction of arrow 464 to the intermediate position 465 and then to final position 463.

To permit motion of the fastener 484 along aperture 418, the fastener 484 is selected with a diameter FDS which is smaller or in clearance with the width W of the central section of 484 of the aperture 418 and which is smaller than both the proximal enlarged section 422 and the distal enlarged section 421.

Figure 17:
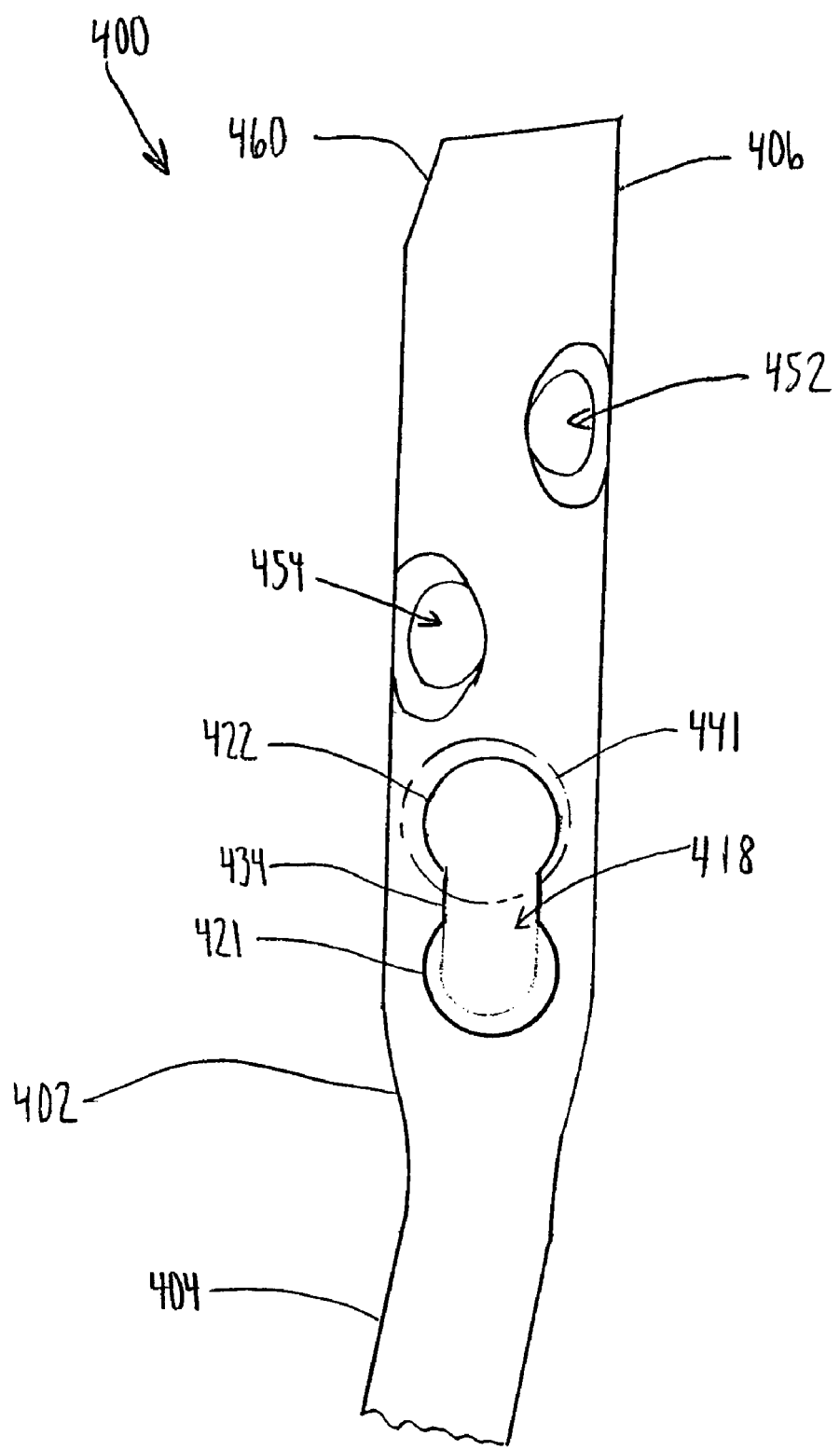
FIG. 17 is a partial plan view of the intramedullary nail of FIG. 7 with the aperture partially filled with a resorbable material.

Referring now to FIG. 17, the nail 400 is shown in use with a plug 441. The plug 441 fills a portion of the aperture 418, and is fitted thereto.

The plug 441 is preferably made of a resorbable and biocompatible material. Many materials fall into this category and include such materials as PLA (polylactic), PGA (polyglyolide) or vitamin E derivatives. Vitamin E derivatives are available and are similar to those materials such as in the DePuy Biostop G product line. The Biostop G material is a mixture of neutral components. These neutral components include glycerol, gelatin and water. This combination of glycerol, gelatin and water may be totally reabsorbed within 15 days of surgery.

Other materials that may be suitable for the plug 441 include monomers and biodegradable polymers.

Monomers include Llactide, Dlactide, DLlactide and glycolide. Llactide is produced by the depolymerization of low molecular weight poly, made by condensation polymerization of the corresponding L(+) lactic acid.

DLlactide is produced by the depolymerization of low molecular weight poly, made by condensation polymerization of the corresponding DLlactic acid.

D(+) lactide is produced by the depolymerization of low molecular weight poly (Dlactic acid), made by condensation polymerization of the corresponding Dlactic acid.

Glycolide is produced by the depolymerization of low molecular weight poly (glycolic acid), made by condensation polymerization of the corresponding glycolic acid (hydroxyacetic acid).

Polymers include two basic categories known as PLA or polylactide. PLA or polylactide include poly(l)lactide (poly (d)lactide, and poly(dl)lactide).

Copolymers include poly(l)lactidecodlactide, poly(l)lactidecodllactide and poly(lactide)coglycolide.

Bioresorbable materials, when in the form of polymers, resorb through the use of two types of biodegradation. The first of this type includes the rapid loss of polymer mass. This type of degradation, when the rate at which the water penetrates the device exceeds that at which the polymer is converted into water-soluble materials, (resulting in erosion throughout the device) is called bulk erosion. All of the commercially available synthetic devices degrade by bulk erosion.

A second type of biodegradation known as surface erosion, occurs when the rate at which the polymer penetrates the device is lower than that of the rate of conversion of the polymer to water-soluble materials. Surface erosion results in the device thinning over time while maintaining its bulk integrity. Polyanhydrides and polyorthoesters are examples of materials that undergo this type of erosion, when the polymer is hydrophobic, but the chemical bonds are highly susceptible to hydrolysis. In general, this process is referred to as bio-erosion rather than biodegradation.

The degradation-absorption mechanism is the result of many interrelated factors, including the stability of the polymer backbone, the presence of catalyst additives and impurities or plasticisers and the geometry of the plug.

Preferably, the plug 441 is designed by utilizing materials and geometry to balance these factors by tailoring a plug to slowly degrade and transfer stress at the appropriate weight to surrounding tissues as they heal.

Applicants believe that a bioresorbable plug may be designed having a resorption rate varying from as little as a few weeks to as long as one year or more. For example, when utilizing vitamin E derivatives such as that of the Biostop G product, resorption rates of a few weeks would occur. Conversely, when using materials such as PLA and PGA the resorption rates may be respectively as great as 6 months or 24 months.

The physical properties of PLA and PGA may be particularly well suited for this application in that PLA has sufficient physical properties to maintain the loads required in such nails. For example, PLA has a tensile strength from 4 to 12,000 psi and PGA has a tensile strength of 10,000 psi or greater.

Preferably, the bioresorbable polymers for use as materials for the plug 441 of the present invention are thermoplastic. These thermoplastic materials can be processed into different product shapes using conventional plastic processing techniques for example, extrusion and injection molding. The process and conditions depend on the particular polymer and inherent viscosity. It is recommended that the polymers be thoroughly dried before processing using suitable drying conditions.

The bioresorbable materials for use in the plug 441 are preferably sterilized. The most commonly used sterilizing methods for such polymers, for example, lactide/glycolide type polymers are gas sterilization (ethylene oxide, ETO) and gamma sterilization. ETO sterilization does not substantially effect the molecular properties of these polymers. Care must be taken that gas residues are sufficiently removed from the material. Gamma radiation is known to result in a significant decrease in the molecular weight of these polymers. This effect should be taken in account during the development phase of the plug.

Due to the biodegradable nature of the polymers for use as materials for the bioresorbable plug (storage conditions below 0° centigrade/32° Fahrenheit should be maintained, preferably at 15° centigrade or 5° Fahrenheit or at a lower temperature. The cold storage serves as an additional precaution against hydrolysis loss. Before use, the package should be allowed to reach room temperature to avoid condensation of atmospheric moisture. When opened, the material should be used as quickly as possible and be sealed, after purging with high purity dry nitrogen, in order to keep out atmospheric moisture.

Referring again to FIG. 17, the plug 441 may be fitted to, for example, the proximal enlarged section 422. The plug 441 may have generally a cylindrical shape to matingly fit the proximal enlarged section 422. The plug 441 may be alternatively fitted into distal elongated section 421. If the plug 441 is positioned in the proximal elongated section 422 a greater amount of dynamization may be possible compared to the movement of the fastener when the plug 441 is positioned in the distal elongated section 421.

Figure 18:
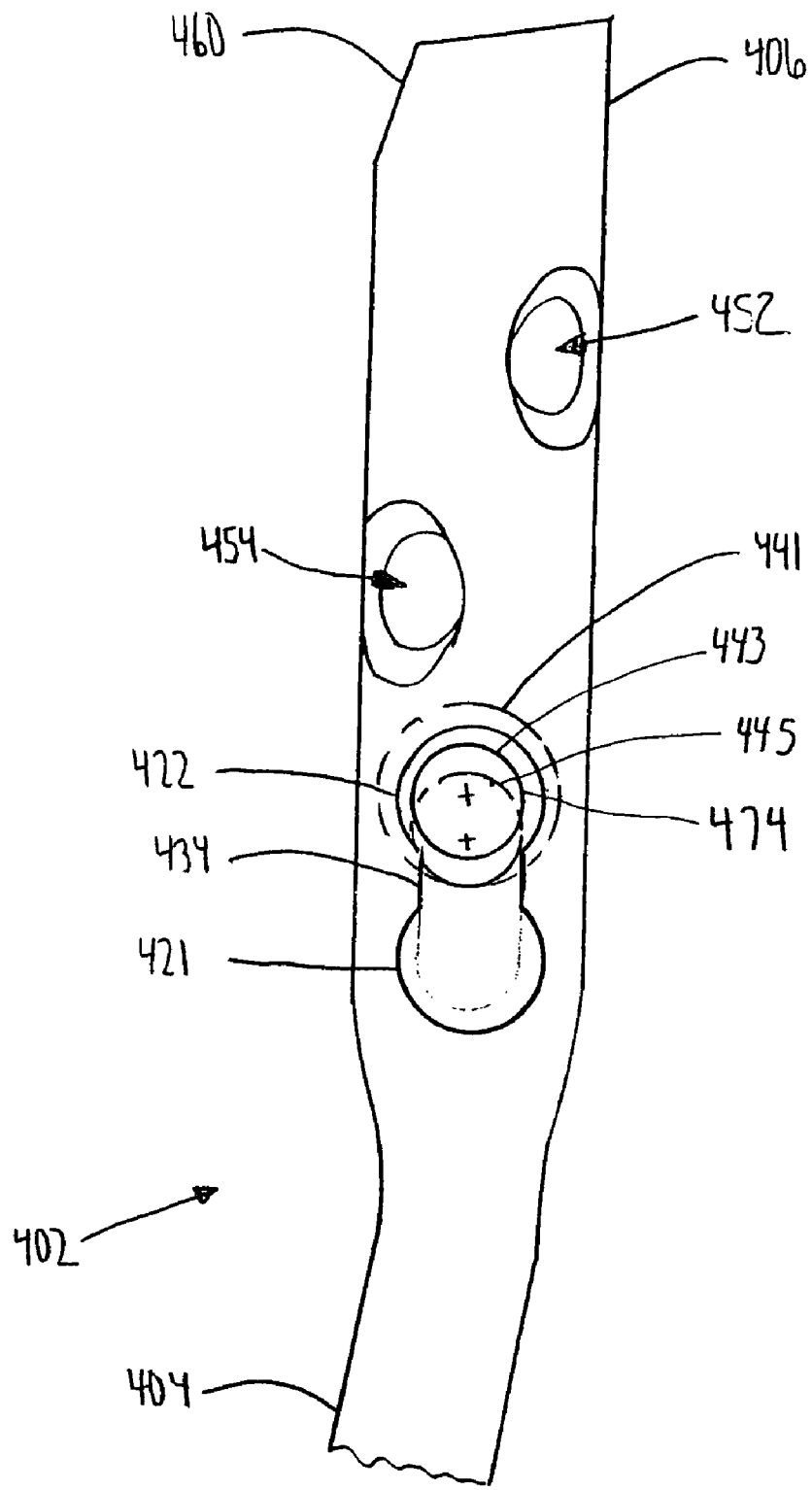
FIG. 18 is a partial plan view of the intramedullary nail of FIG. 17 showing a threaded fastener in the material and positioned spaced from the walls of the aperture to permit limited dynamzation.

Referring now to FIG. 18, the plug 441 is shown in position on the nail 400 and a fastener for example, fastener 474 is shown in position in the plug 441. As shown in FIG. 18 the fastener 474 may be positioned centrally within the plug 441 at first position 443. As the plug 441 biodegrades the fastener 474 may migrate under dynamization to second position 445 shown in phantom.

Figure 19:
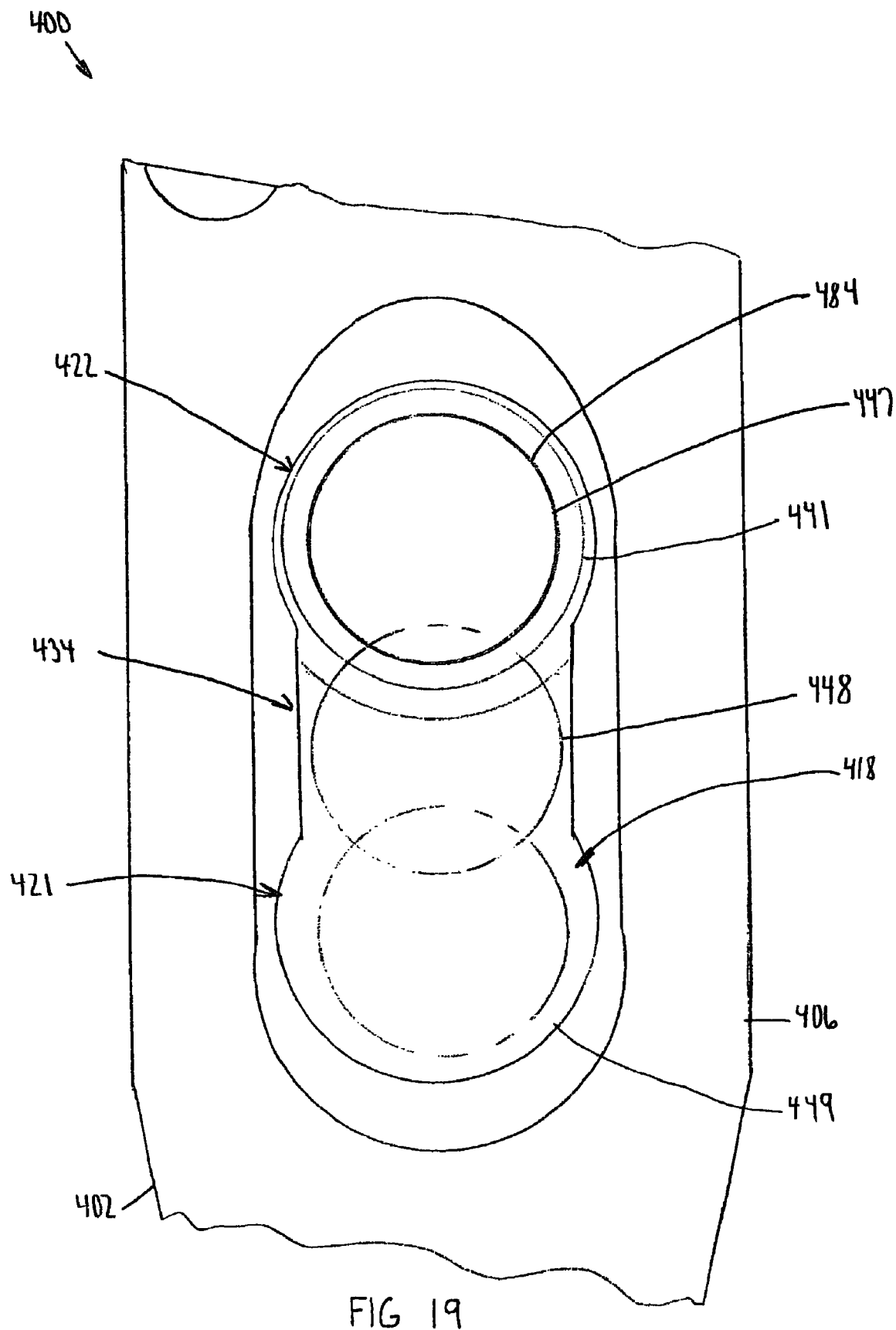
FIG. 19 is an enlarged partial plan view of the intramedullary nail and fastener assembly of FIG. 18 showing the movement of the fastener during resorbsion and dynamazation.
Figure 2D:
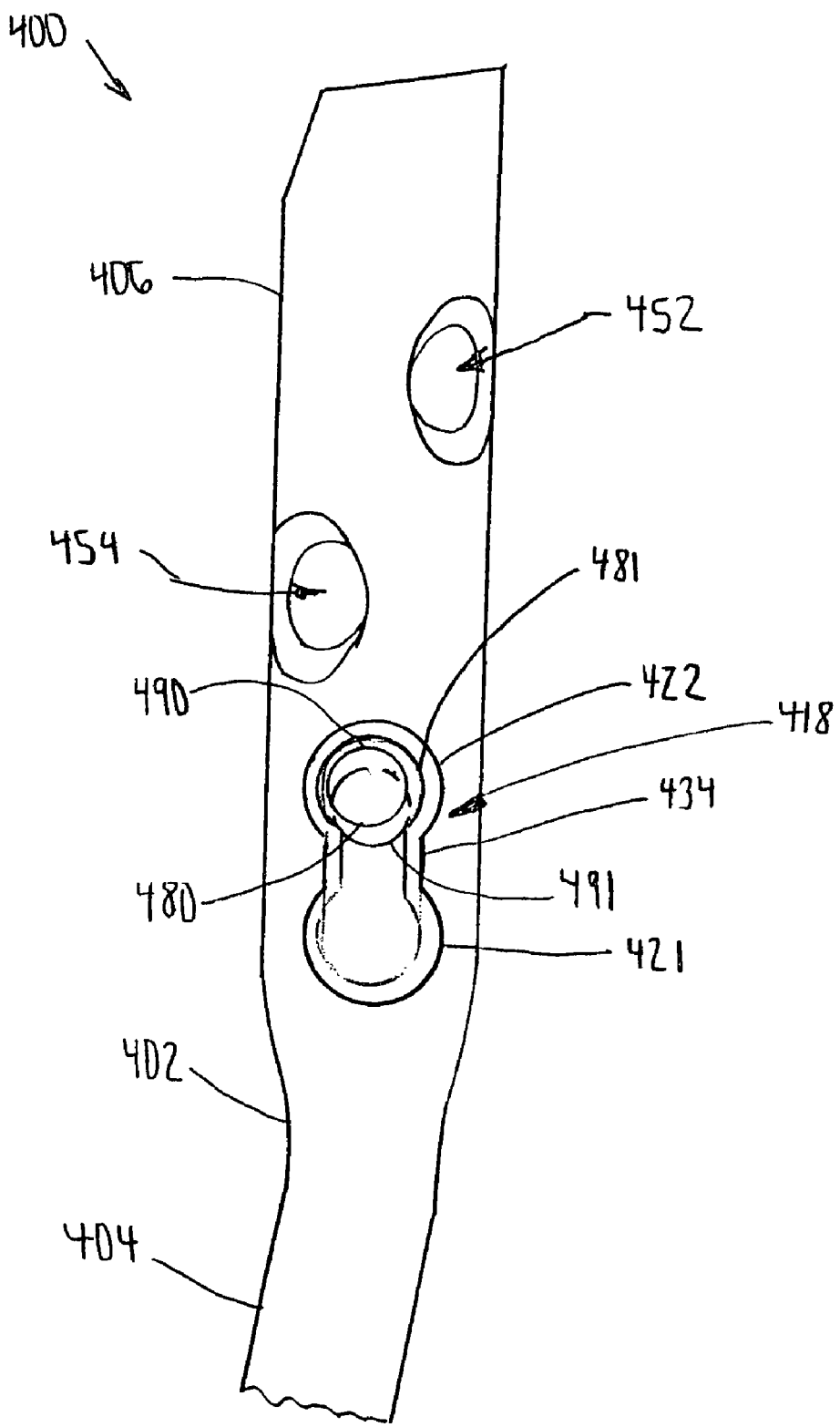

Referring now to FIG. 19, the nail 400 is shown in use with plug 441 as well as with the smaller fastener 484. The screw 484 permits full dynamization from first position 447 (shown in solid) to intermediate position 448 and to final position 449, both shown in phantom. The first position of 447 of fastener 484 is centrally located within the proximal section 422 and within the plug 441. As the plug 441 resorbs the screw 484 migrates from first position 447 to the intermediate position 448. At the intermediate position 448, the plug 441 is fully resorbed and the motion to intermediate position 448 to final position 449 is controlled by the dynamization of the fracture site.

Referring now to FIG. 20, another embodiment to the current invention is shown as the nail 400 in use with full resorbable plug 481. The fully resorbable plug 481 may fit a sufficient portion or substantially the entire aperture 418. The resorbable plug 481 may be pressed or slip fitted into aperture 418 and be made of any suitable, durable, material such as that of plug 441 as previously described. The resorbable plug 481 may be used for partially dynamization as well as for full dynamization.

Referring to FIG. 20, the plug 481 may be used with partial dynamization. For example, the fastener 480 may be positioned in the center of, for example, the proximal enlarged section 422. The fastener 480 may move from first position 490 (shown in solid) to second position 492 (shown in phantom). It should be appreciated that fastener 480 may be positioned in the distal enlarged section 421 as well to provide for some limited dynamization.

Figure 21:
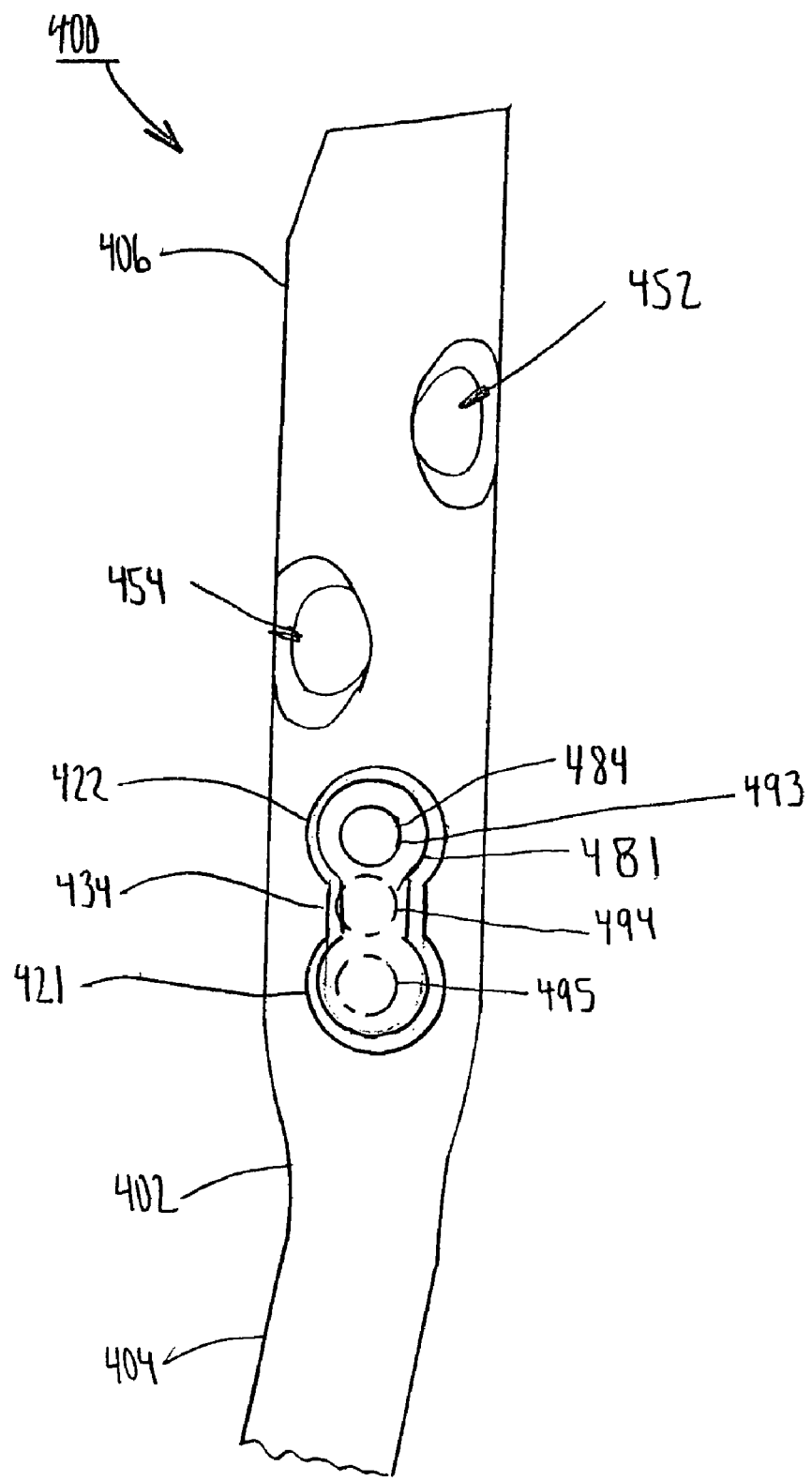
FIG. 21 is a partial plan view of the intramedullary nail of FIG. 20 showing a smaller threaded fastener in the material and positioned in the aperture to permit full dynamization along the length of the aperture.
Figure 21:
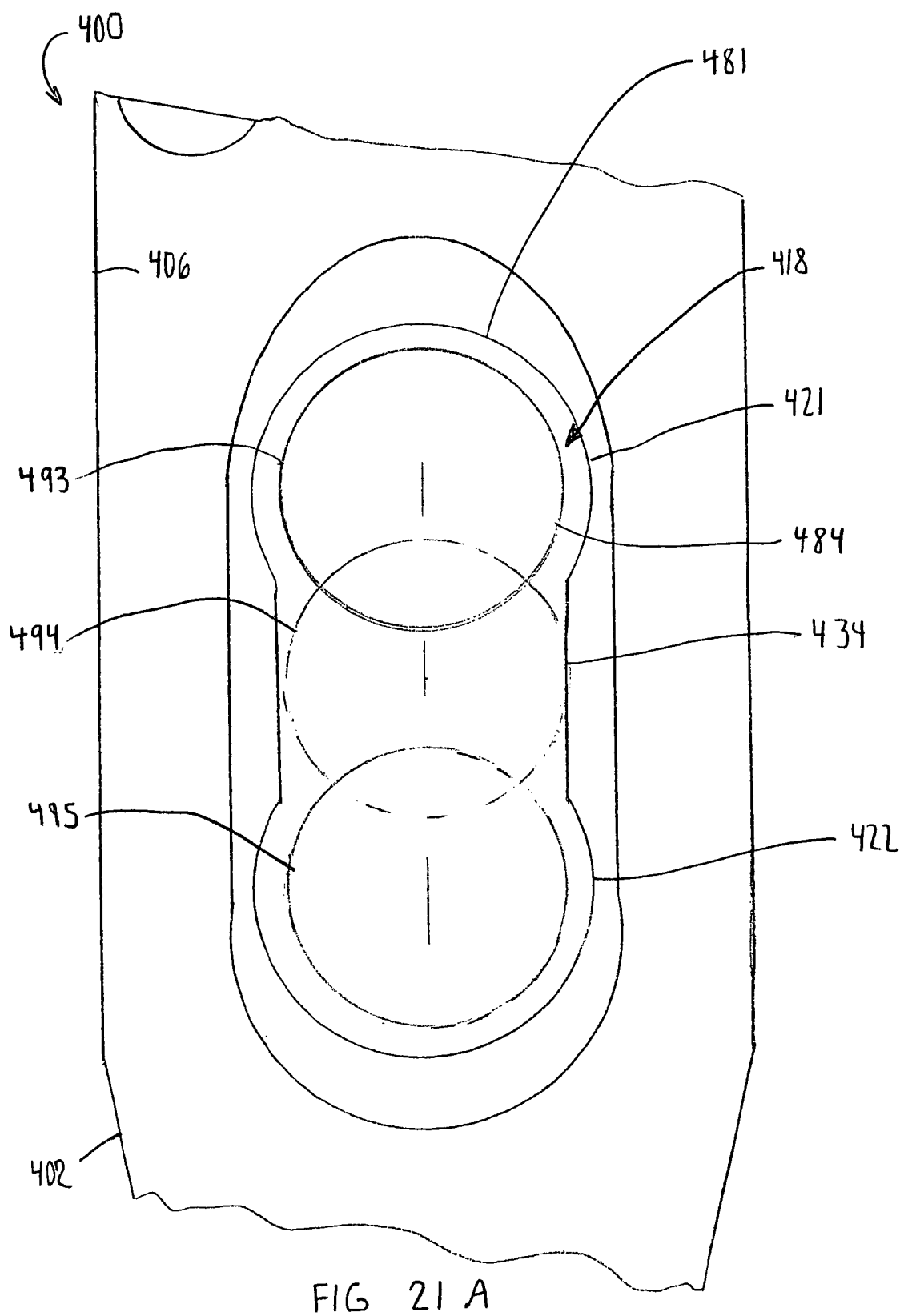

Referring now to FIGS. 21 and 21A, the absorbable plug 481, may be used in the nail 400 with use for a full dynamization. For use with full dynamization, the nail 400 is used with a smaller fastener, for example, fastener 484 as shown in FIGS. 21 and 21A. The fastener 484 may be positioned centrally within proximal elongated section 422 of the aperture 418 in first position 493. Under dynamization and resorption the fastener 484 moves to second position 494 (as shown in phantom) and finally to position 495 (also shown in phantom).

Figure 22:
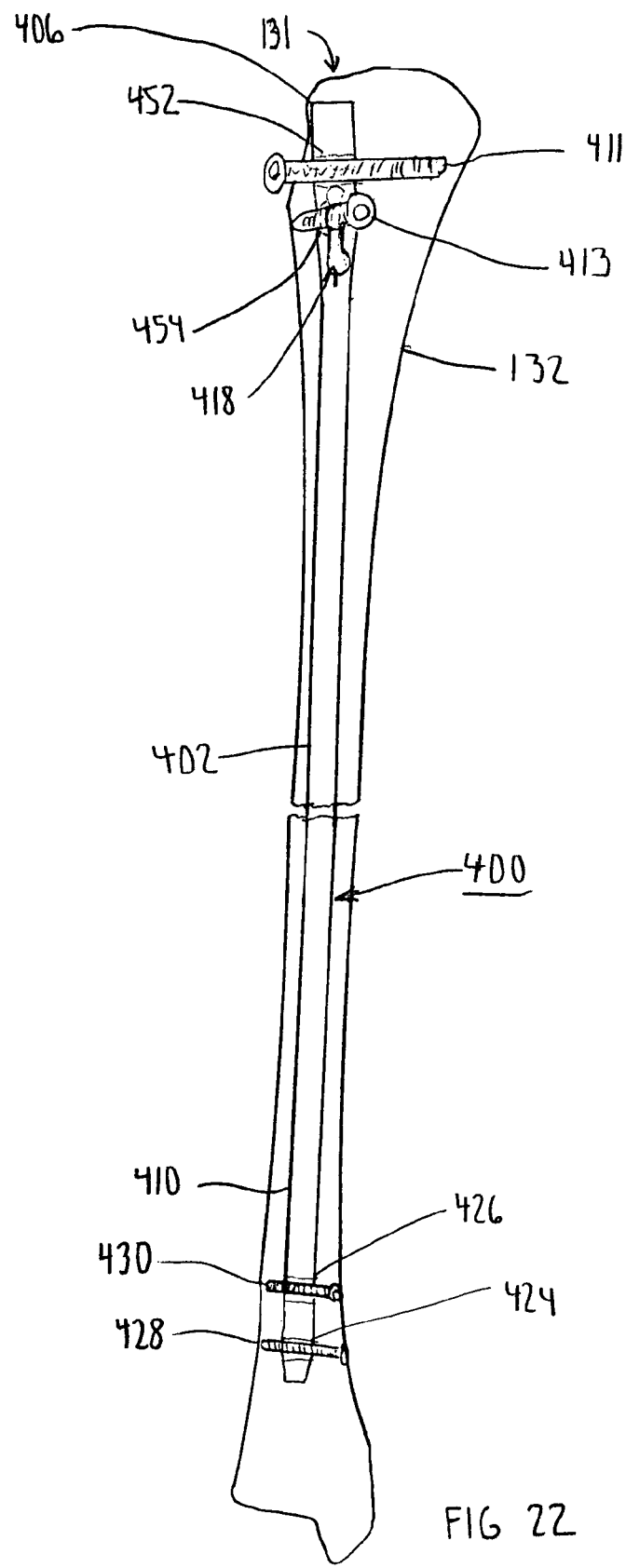
FIG. 22 is a plan view partially in cross section of the intramedullary nail of FIG. 7 showing the nail in position in a tibia.

Referring now to FIG. 22, the nail 400 is shown in position in canal 131 of the long bone or tibia 132. It should be appreciated that the nail 400 of the present invention may include fasteners in addition to those previously mentioned for cooperation with aperture 418. To properly position the nail 400 within the canal 131 of the tibia 132, a first distal fastener 428 may be associated with, for example, the first distal cross-hole 424. It should be appreciated that a second distal fastener, for example, fastener 430, may be positioned in the second distal cross-hole 426. The distal fasteners 428 and 430 may, for example, be similar to the fasteners 121 and 123 of the nail 100 of FIG. 5.

To permit dynamization, the proximal portion 406 of the nail 400 may include only fasteners associated with the aperture 418. If the nail 400 is utilized without dynamization, for example, if used as a static nail, additional fasteners may be provided in the proximal portion 406 of the nail 400. For example, a first proximal fastener 411 may be associated with the first proximal hole 452. Similarly a second proximal fastener 413 may be associated with the second proximal hole 454. The first and second proximal fasteners 411 and 413 may be similar to fasteners 111 and 113 of the nail 100 of FIG. 5.

Figure 23:
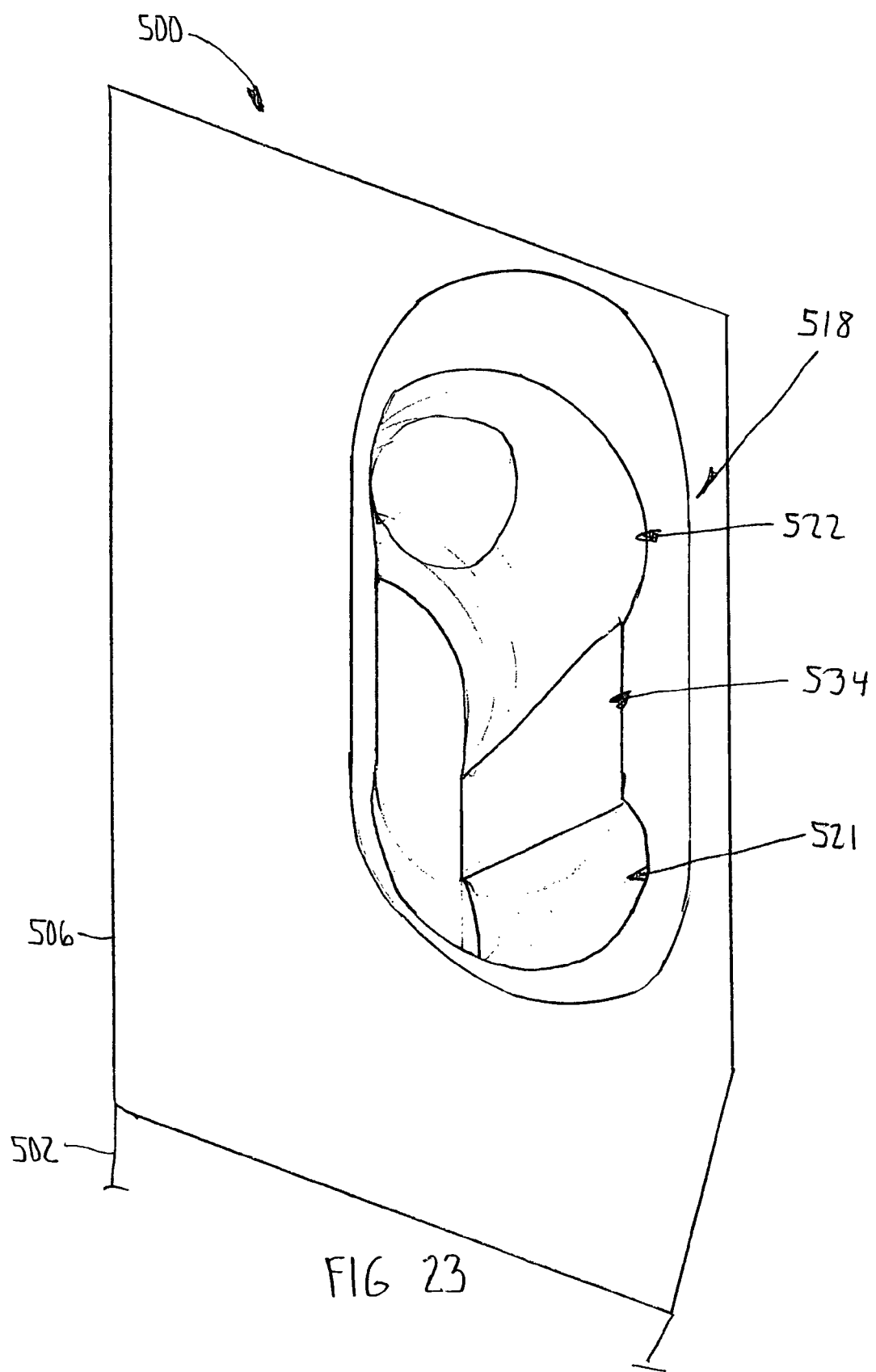
FIG. 23 is a partial perspective an intramedullary nail with an aperture in the end of the nail having no threads and having two opposed cylindrical areas in accordance with a further embodiment of the present invention.

Referring now to FIG. 23, another embodiment of the current invention is shown as nail 500. Nail 500 is similar to nail 400 of FIGS. 8-22 and includes a proximal portion 506 of body 502. The proximal portion 506 is similar to the portion 406 of the nail 400 of FIGS. 8-22 and includes an aperture 518 having a proximal section 522, a central section 534, and a distal section 521. The proximal section 522 and the distal section 521 are different than the corresponding proximal section 422 and distal section 421 of the aperture 418 of the nail 400 in that the proximal section 522 and the distal section 521 do not include threads. The nail 500 may provide axial rigidity while permitting radial cross movement of the fastener within the nail 500.

Figure 23A:
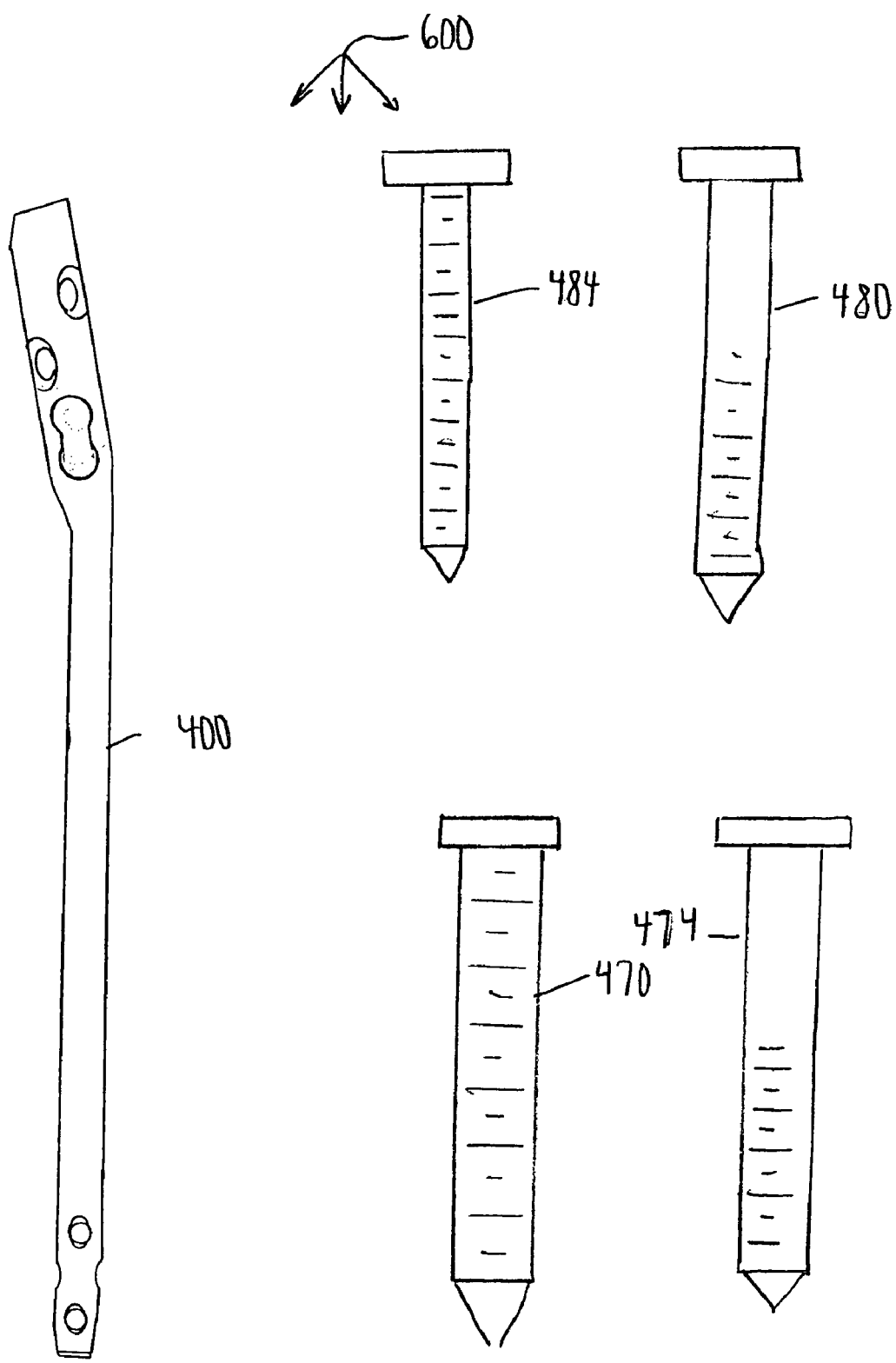
FIG. 23A is a plan view of a kit including a nail and a plurality of fasteners in accordance with a further embodiment of the present invention.

Referring now to FIG. 23A, another embodiment of the current invention is shown as kit 600. Kit 600 includes, for example, the nail 400 as well as a fastener, for example, fastener 470. The kit 600 may further include a second fastener, for example fastener 484. The kit 600 may further include a third fastener, for example, fastener 474. The kit 600 may also include a fourth fastener, for example, fastener 480. The fasteners 484, 480, 470, and 474 may be positioned in the proximal enlarged section 422 or the distal enlarged section 421.

It should be appreciated that the nail of the present invention with the elongated aperture may be utilized with any long bone. Referring now to FIG. 24, another embodiment of the present invention is shown as nail 700. The nail 700 is in the form of a femoral nail for use in femur 702 and includes an elongated opening 718.

Referring now to FIG. 25, the present invention is shown as a retrograde nail 800 including an elongated opening 818 for use with a femur 702.

Figures 26, 27:
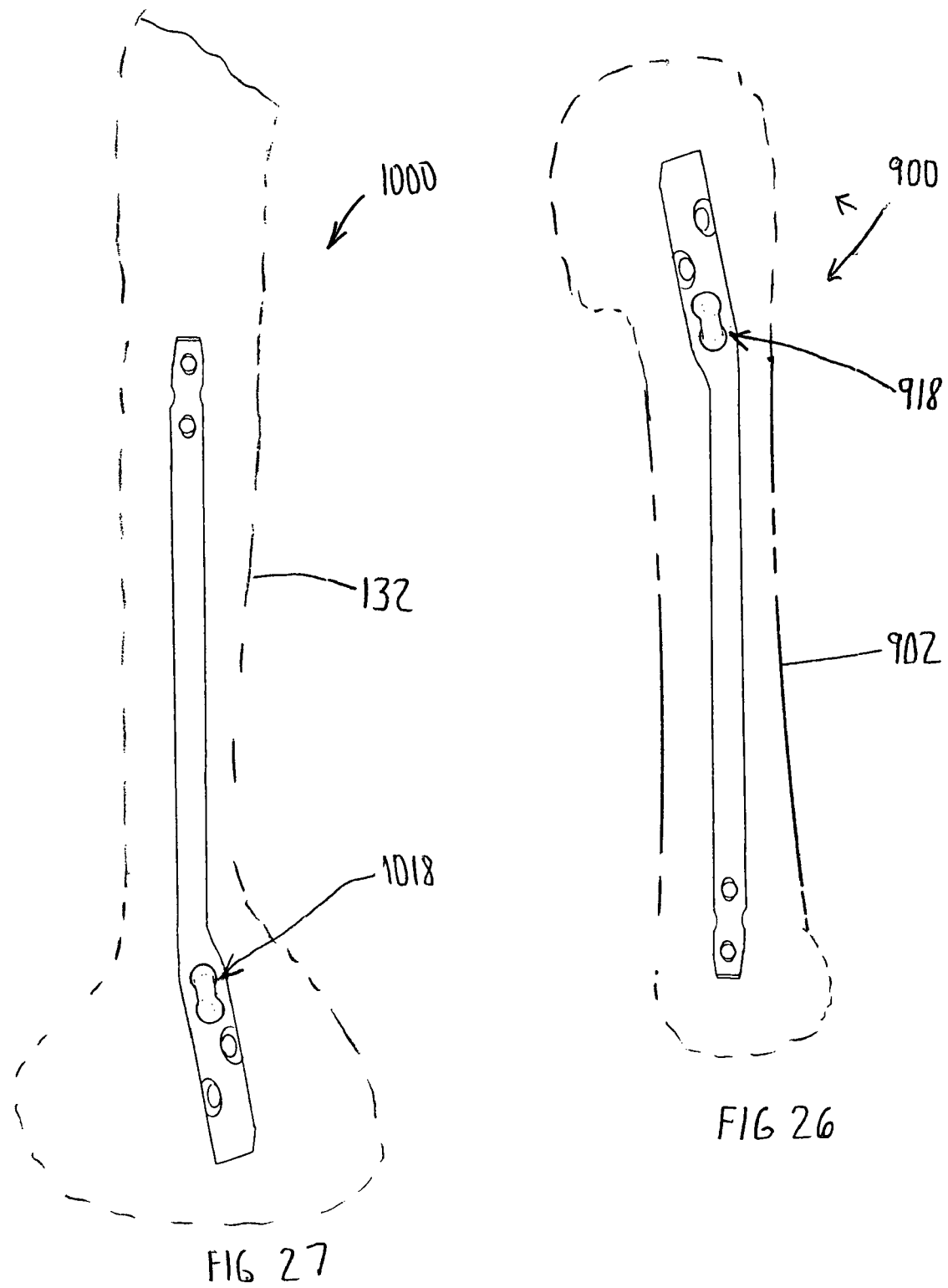
FIG. 26 is a plan view partially in cross section of the intramedullary nail of the present invention showing the nail in position in a humerus in the form of a humeral nail.
FIG. 27 is a plan view partially in cross section of the intramedullary nail of the present invention showing the nail in position in a tibia in the form of a supercondyral nail.

Referring now to FIG. 26, another embodiment of the form humeral nail 900 is shown. The humeral nail 900 includes an elongated opening 918 for use with a humerus 902.

Referring now to FIG. 27, another embodiment of the present invention is shown as supercondyral nail 1000. Supercondyral nail 1000 is used with, for example, tibia 132. The nail 1000 includes an elongated opening 1018.

Figure 28:
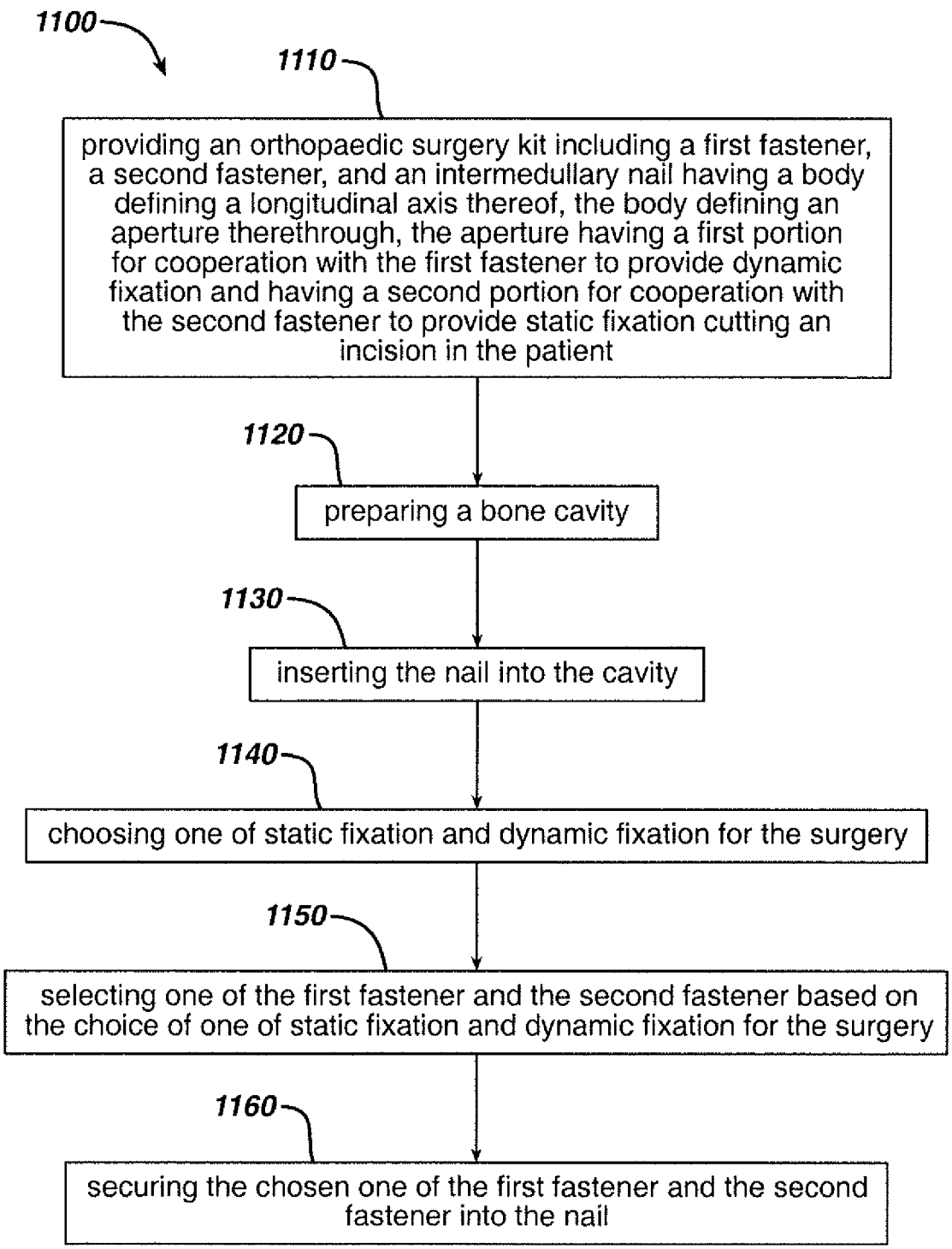
FIG. 28 is a flow chart of a method for performing trauma surgery in accordance with yet another embodiment of the present invention.

Referring now to FIG. 28, another embodiment to the present invention is shown as method 1100 to perform arthroplasty. The method 1100 includes a first step 1110 of providing an orthopaedic surgery kit including a first fastener, a second fastener, and intramedullary nail having a body. The body defines the longitudinal axis of the body. The body also defines an aperture through the body. The aperture has a first portion of cooperation with a first a fastener to provide dynamic fixation, and has a second portion for cooperation with the second fastener to provide static fixation for cutting an incision in the patient.

The method 1100 further includes a second step 1120 of preparing a bone cavity. The method also includes a third step 1130 of inserting the nail into the cavity. The method 1100 further includes a fourth step 1140 of choosing one of static fixation and dynamic fixation for the surgery and a fifth step 1150 of selecting one of the first fastener and the second fastener based upon the choice of static fixation or dynamic fixation for the surgery. The method includes a sixth step 1160 of securing the chosen one of a first fastener and a second fastener into the nail.

Although the present invention and its advantages have been described in detail, it should be understood that various changes, substitutions, and alterations can be made therein without departing from the spirit and scope of the present invention as defined by the appended claims.

I claim:

1. A kit for use in orthopaedic surgery, the kit comprising:
a first fastener comprising a shank having maximum outer diameter;
a second fastener comprising a shank having a maximum outer diameter; and
an intramedullary nail comprising a body having two ends and an edge defining an aperture therethrough, the edge being spaced from the two ends and including first substantially parallel parts defining a first portion of the aperture sized and shaped to cooperate with said first fastener to provide dynamic fixation and a second curved part extending from and connected to said first substantially parallel parts defining a curved portion of the aperture sized and shaped to cooperate with said second fastener to provide one of static fixation and dynamic fixation, the second curved portion of the aperture having a width greater than the distance between the first substantially parallel parts of the edge defining the first portion of the aperture, the aperture being symmetrical about a longitudinal axis extending from the second curved portion and between the substantially parallel parts;
wherein the maximum outer diameter of the shank of the first fastener is less than the distance between the first substantially parallel parts of the edge defining the first portion of the aperture; and
wherein the maximum outer diameter of the shank of the second fastener is greater than the distance between the first substantially parallel parts of the edge defining the first portion of the aperture.

2. The kit of claim 1, wherein the first substantially parallel edges of the aperture define a rectangular central section and the second curved portion of the aperture defines a cylindrical end section adjoining the rectangular central section.

3. The kit of claim 2, wherein the aperture further includes a second cylindrical end section opposed to the first mentioned cylindrical end section.

4. The kit of claim 3:
wherein said body adjacent the first mentioned cylindrical end defines internal threads therein; and
wherein said body adjacent the second cylindrical end defines internal threads therein.

5. The kit of claim 2, wherein the cylindrical end section is adapted to matingly fit with the second fastener.

6. The kit of claim 2, wherein the cylindrical end section is adapted to one of slidable fit and threadable fit with the second fastener.

7. The kit of claim 1, wherein the body has a longitudinal axis extending through at least one of the ends of the body and wherein the aperture is adapted to provide for a slidable fit of the first fastener with said body along the longitudinal axis of said body.

8. The kit of claim 1, further comprising a resorbable component for cooperation with said body adjacent the aperture.

9. The kit of claim 8:
wherein said body comprises internal threads formed in the body adjacent the aperture; and
wherein said resorbable component comprises external threads formed thereon for cooperation with the internal threads of said body.

10. The kit of claim 1, wherein the aperture defines a slot axis thereof, the slot axis being perpendicular to the longitudinal axis of said body.

11. The kit of claim 1 further comprising a third fastener including a shank having a maximum outer diameter less than the width of the curved portion of the aperture and greater than the distance between the first substantially parallel parts of the edge defining the first portion of the aperture.

12. A kit for use in orthopaedic surgery, the kit comprising a first fastener including a shank having a maximum outer diameter, a second fastener including a shank having a maximum outer diameter, a third fastener including a shank having a maximum outer diameter, and an intramedullary nail comprising: a body having a first end, a second end and an edge defining an aperture therethrough, the edge defining the aperture being spaced from the first and second ends and having a curved part and opposed straight parts, the curved part of the edge extending for more than 180 degrees, the aperture defining an enlarged portion thereof along the curved edge, the enlarged portion having a diameter, the aperture having a constricted portion adjacent and connected to the enlarged portion defined by the two opposing straight parts of the edge, the diameter of the enlarged portion being greater than the distance between the two opposing parts of the edge defining the constricted portion of the aperture, the aperture being symmetrical about an axis through the enlarged portion and constricted portion;
wherein the maximum outer diameter of the shank of the first fastener is less than the distance between the two opposing parts of the edge defining the constricted portion of the aperture to allow for dynamic fixation when the first fastener is used with the intramedullary nail;
wherein the maximum outer diameter of the shank of the second fastener is great enough to allow for static fixation when the second fastener is placed in the enlarged portion of the aperture;
wherein the maximum outer diameter of the shank of the third fastener is less than the maximum outer diameter of the shank of the second fastener and greater than the distance between the two opposing parts of the edge defining the constricted portion of the aperture;
wherein the first fastener and the constricted portion of the aperture are sized to allow for dynamic fixation with a degree of relative movement allowable between bone parts and the third fastener and the enlarged portion of the aperture are sized to allow for dynamic fixation with a lesser degree of relative movement allowable between bone parts.

13. The intramedullary nail of claim 12:
wherein the aperture has a rectangular central section; and
wherein the enlarged portion is in the form of a generally cylindrical section and is positioned adjacent an end of the rectangular central section of the aperture.

14. The intramedullary nail of claim 13:
wherein the cylindrical section of said body is adapted to matingly fit with said second fastener.

15. The intramedullary nail of claim 14, wherein the cylindrical section is adapted to slidably fit with said first and third fasteners and threadably fit with said second fastener.

16. The intramedullary nail of claim 14, wherein the body has a longitudinal axis extending through at least one of the first and second ends and wherein the aperture is adapted to provide for a slidable fit of said fastener with said body along the longitudinal axis of said body.

17. The intramedullary nail of claim 13, wherein the aperture further includes a second enlarged cylindrical section opposed to the first mentioned cylindrical section.

18. The intramedullary nail of claim 17:
wherein said body adjacent the first mentioned cylindrical section defines internal threads therein; and
wherein said body adjacent the second cylindrical section defines internal threads therein.

19. The intramedullary nail of claim 12, further comprising a resorbable component for cooperation with said body adjacent the aperture.

20. The intramedullary nail of claim 19:
wherein said body comprises internal threads formed in the body adjacent the aperture; and
wherein said resorbable component comprises external threads formed thereon for cooperation with the internal threads of said body.

21. The intramedullary nail of claim 12, wherein the enlarged portion is adjacent an end of the aperture.

* * * * *